US009582465B2

(12) United States Patent
Hyde et al.

(10) Patent No.: US 9,582,465 B2
(45) Date of Patent: Feb. 28, 2017

(54) FLEXIBLE PROCESSORS AND FLEXIBLE MEMORY

(71) Applicant: Elwha LLC, a limited liability corporation of the State of Delaware, Bellevue, WA (US)

(72) Inventors: Roderick A. Hyde, Redmond, WA (US); Nicholas F. Pasch, Bellevue, WA (US); Clarence T. Tegreene, Mercer Island, WA (US)

(73) Assignee: Elwha LLC, Bellevue, WA (US)

( * ) Notice: Subject to any disclaimer, the term of this patent is extended or adjusted under 35 U.S.C. 154(b) by 58 days.

(21) Appl. No.: 13/691,448

(22) Filed: Nov. 30, 2012

(65) Prior Publication Data

US 2014/0136755 A1 May 15, 2014

Related U.S. Application Data

(63) Continuation-in-part of application No. 13/687,983, filed on Nov. 28, 2012, now Pat. No. 8,996,951, which is a continuation-in-part of application No. 13/678,439, filed on Nov. 15, 2012, now Pat. No. 8,966,310, which is a continuation-in-part of application No. 13/678,430, filed on Nov. 15, 2012, now Pat. No. 9,026,719.

(51) Int. Cl.
*A61B 5/00* (2006.01)
*G06F 15/78* (2006.01)

(52) U.S. Cl.
CPC ........ *G06F 15/7814* (2013.01); *A61B 5/6801* (2013.01); *A61B 5/6846* (2013.01); *Y02B 60/1207* (2013.01); *Y02B 60/1225* (2013.01)

(58) Field of Classification Search
CPC ....... A61B 5/0002–5/0031; A61B 5/02; A61B 5/021–5/02125; A61B 5/02438; A61B 5/026; A61B 5/0476–5/0484; A61B 5/145–5/14865

See application file for complete search history.

(56) References Cited

U.S. PATENT DOCUMENTS

| | | | |
|---|---|---|---|
| 5,303,163 A | * | 4/1994 | Ebaugh et al. ............... 700/274 |
| 5,533,123 A | | 7/1996 | Force et al. |
| 6,215,326 B1 | | 4/2001 | Jefferson et al. |
| 6,366,117 B1 | | 4/2002 | Pang et al. |
| 6,708,273 B1 | | 3/2004 | Ober et al. |
| 7,100,071 B2 | | 8/2006 | Olarig |
| 7,133,498 B2 | * | 11/2006 | Cacioppo et al. ............. 379/45 |
| 7,177,199 B2 | | 2/2007 | Chen et al. |

(Continued)

OTHER PUBLICATIONS

Chi et al.; "Processing-in-Memory in ReRAM-based Main Memory"; SEAL-lab Technical Report; bearing a date of Nov. 30, 2015; pp. 1-11; No. 2015-001.

(Continued)

*Primary Examiner* — Yaima Rigol
*Assistant Examiner* — Tasnima Matin

(57) ABSTRACT

An apparatus includes but is not limited to a non-volatile memory array and a processor integrated with the apparatus. The processor is operable to operate in combination with the non-volatile memory array to accumulate information associated with a product. In addition to the foregoing, other aspects are described in the claims, drawings, and text forming a part of the present disclosure.

42 Claims, 29 Drawing Sheets

(56) References Cited

U.S. PATENT DOCUMENTS

| | | | |
|---|---|---|---|
| 7,195,776 B2* | 3/2007 | Helmus | A61K 9/0024 424/422 |
| 7,203,842 B2 | 4/2007 | Kean | |
| 7,890,691 B2 | 2/2011 | Jiang | |
| 7,996,642 B1* | 8/2011 | Smith | 711/167 |
| 8,015,357 B2 | 9/2011 | Strumper et al. | |
| 8,131,915 B1 | 3/2012 | Yang | |
| 8,171,204 B2 | 5/2012 | Chow et al. | |
| 8,572,311 B1 | 10/2013 | Shalvi et al. | |
| 8,880,980 B1 | 11/2014 | Mathew et al. | |
| 8,893,267 B1 | 11/2014 | Sathe et al. | |
| 8,935,493 B1 | 1/2015 | Dolan et al. | |
| 2003/0071734 A1* | 4/2003 | Vodin | F41H 9/00 340/573.1 |
| 2004/0015674 A1* | 1/2004 | Lakhani et al. | 711/206 |
| 2004/0039845 A1 | 2/2004 | Feldmeier et al. | |
| 2004/0236954 A1* | 11/2004 | Vogt et al. | 713/186 |
| 2006/0186473 A1 | 8/2006 | Mech et al. | |
| 2006/0219776 A1* | 10/2006 | Finn | 235/380 |
| 2006/0259848 A1 | 11/2006 | Blevins | |
| 2007/0040195 A1 | 2/2007 | Auciello | |
| 2007/0045425 A1 | 3/2007 | Yoshida et al. | |
| 2007/0100219 A1* | 5/2007 | Sweitzer | A61B 5/0002 600/323 |
| 2007/0121575 A1 | 5/2007 | Savry et al. | |
| 2007/0129812 A1* | 6/2007 | Ferchau | 700/1 |
| 2007/0136534 A1 | 6/2007 | Mesard et al. | |
| 2007/0177042 A1 | 8/2007 | He et al. | |
| 2007/0191728 A1* | 8/2007 | Shennib | A61B 5/0006 600/546 |
| 2007/0234323 A1 | 10/2007 | Franaszek et al. | |
| 2007/0294494 A1* | 12/2007 | Conti et al. | 711/158 |
| 2008/0082766 A1 | 4/2008 | Okin et al. | |
| 2008/0090322 A1 | 4/2008 | Mech et al. | |
| 2008/0144349 A1* | 6/2008 | Kato | B82Y 10/00 365/103 |
| 2009/0089492 A1 | 4/2009 | Yoon et al. | |
| 2009/0165086 A1 | 6/2009 | Trichina et al. | |
| 2009/0234916 A1* | 9/2009 | Cosentino et al. | 709/203 |
| 2009/0259265 A1 | 10/2009 | Stevenson et al. | |
| 2009/0289323 A1* | 11/2009 | Tessitore | G06F 1/3203 257/506 |
| 2009/0292871 A1 | 11/2009 | Watanabe et al. | |
| 2009/0300238 A1 | 12/2009 | Panabaker et al. | |
| 2010/0027788 A1 | 2/2010 | Tkacik et al. | |
| 2010/0049751 A1 | 2/2010 | Giampaolo et al. | |
| 2010/0064111 A1 | 3/2010 | Kunimatsu et al. | |
| 2010/0070549 A1 | 3/2010 | Nagaraj | |
| 2010/0103716 A1 | 4/2010 | Zheng | |
| 2010/0115330 A1 | 5/2010 | Khatri et al. | |
| 2010/0148232 A1* | 6/2010 | Ng et al. | 257/295 |
| 2010/0174849 A1 | 7/2010 | Walston et al. | |
| 2010/0241787 A1 | 9/2010 | Goldman et al. | |
| 2010/0262773 A1* | 10/2010 | Borchers et al. | 711/114 |
| 2010/0293317 A1 | 11/2010 | Confalonieri et al. | |
| 2011/0022932 A1 | 1/2011 | Radke | |
| 2011/0069539 A1 | 3/2011 | Eleftheriou et al. | |
| 2011/0093670 A1 | 4/2011 | Cherian | |
| 2011/0093675 A1 | 4/2011 | Lu et al. | |
| 2011/0172498 A1* | 7/2011 | Olsen et al. | 600/300 |
| 2011/0224665 A1* | 9/2011 | Crosby et al. | 606/33 |
| 2011/0254987 A1 | 10/2011 | Massetti | |
| 2012/0079318 A1* | 3/2012 | Colgrove et al. | 714/6.22 |
| 2012/0096215 A1 | 4/2012 | Zhang et al. | |
| 2012/0147937 A1* | 6/2012 | Goss et al. | 375/222 |
| 2012/0172085 A1* | 7/2012 | Vuppu et al. | 455/556.1 |
| 2012/0179735 A1 | 7/2012 | Ferguson et al. | |
| 2012/0198152 A1 | 8/2012 | Terry et al. | |
| 2012/0224425 A1 | 9/2012 | Fai et al. | |
| 2012/0233231 A1 | 9/2012 | Vasyltsov et al. | |
| 2012/0233232 A1 | 9/2012 | Vergnes et al. | |
| 2012/0260023 A1 | 10/2012 | Nagai et al. | |
| 2012/0265923 A1 | 10/2012 | Kuo et al. | |
| 2012/0278584 A1 | 11/2012 | Nagami et al. | |
| 2012/0311237 A1 | 12/2012 | Park | |
| 2013/0007374 A1 | 1/2013 | Cain, III et al. | |
| 2013/0013864 A1 | 1/2013 | Chung et al. | |
| 2013/0290792 A1 | 10/2013 | Torla et al. | |
| 2013/0304979 A1 | 11/2013 | Zimmer et al. | |
| 2013/0332705 A1 | 12/2013 | Martinez et al. | |
| 2014/0006898 A1 | 1/2014 | Sharon et al. | |
| 2014/0040338 A1 | 2/2014 | Van Der Sluis et al. | |
| 2014/0040532 A1 | 2/2014 | Watanabe et al. | |
| 2014/0104966 A1 | 4/2014 | Oh et al. | |
| 2014/0136583 A1 | 5/2014 | Hyde et al. | |
| 2014/0143593 A1 | 5/2014 | Strauss et al. | |

OTHER PUBLICATIONS

Hamdioui et al.; "Memristor Based Computation-in-Memory Architecture for Data-Intensive Applications"; Design, Automation & Test in Europe Conference & Exhibition: Mar. 9-13, 2015 (Date 2015, France); European Design and Automation Association (EDAA); bearing a date of 2015 (created on Jul. 6, 2016); pp. 1718-1721.

* cited by examiner

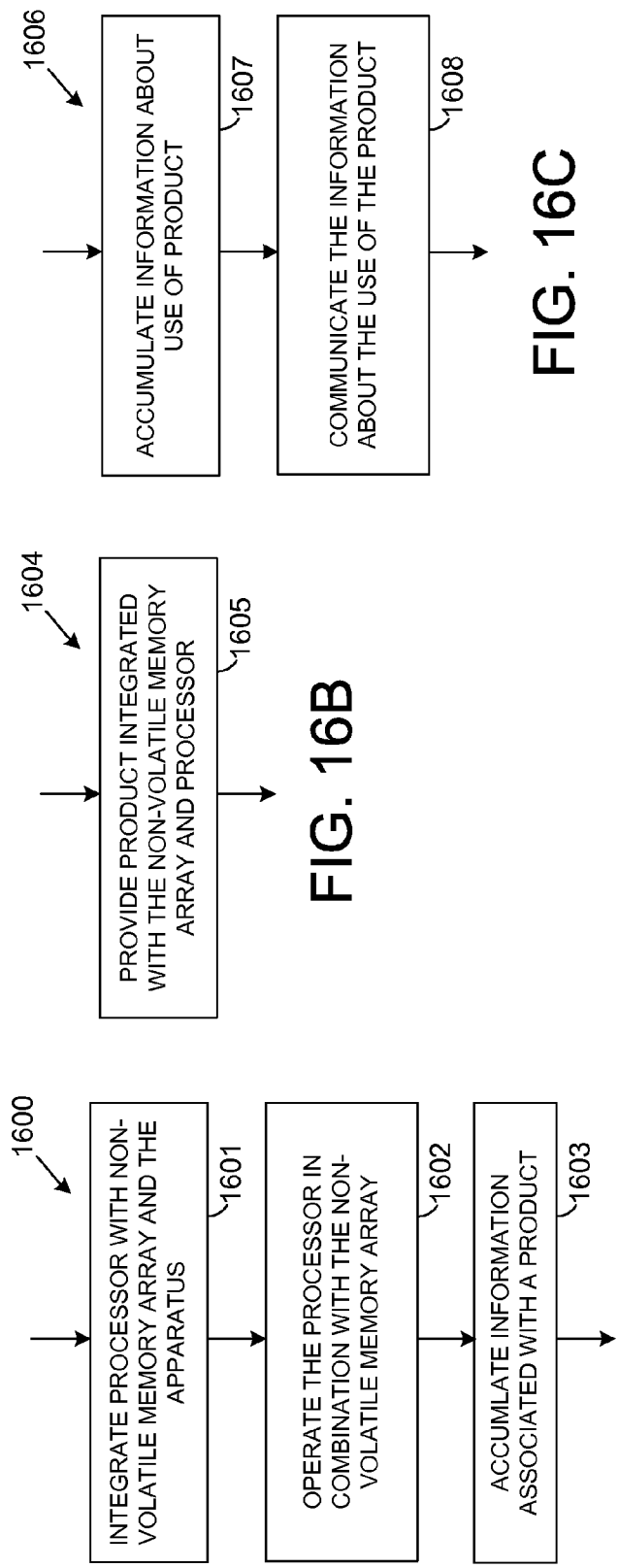

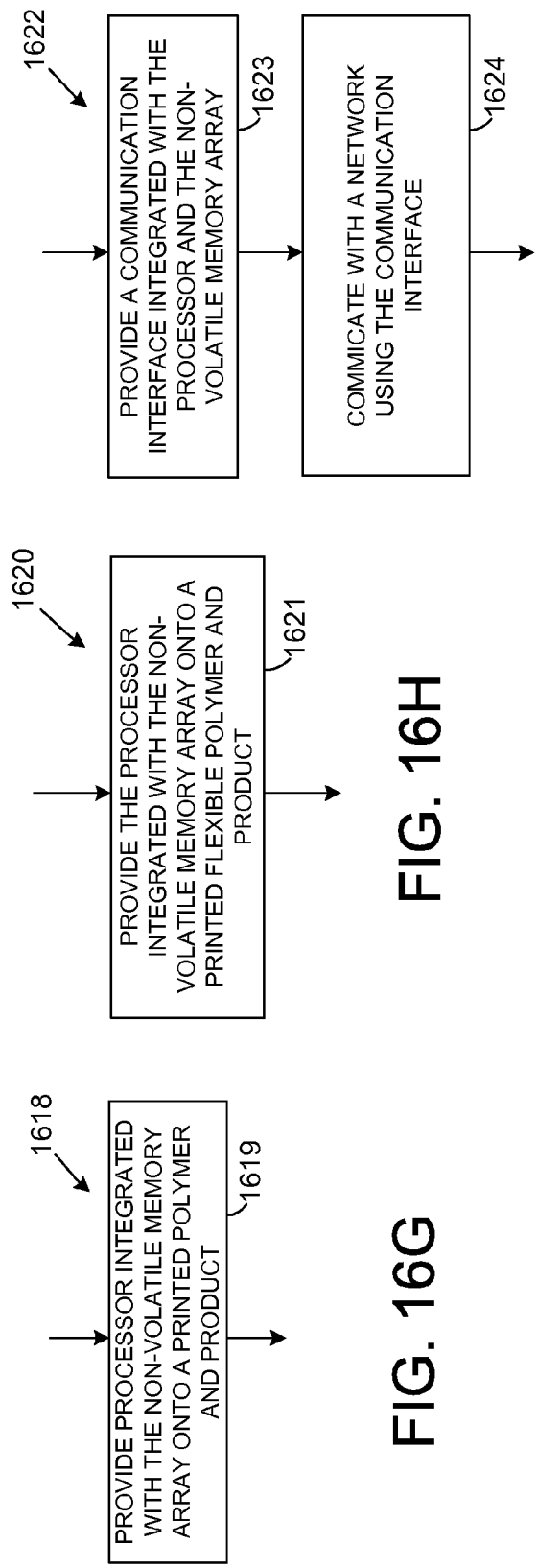

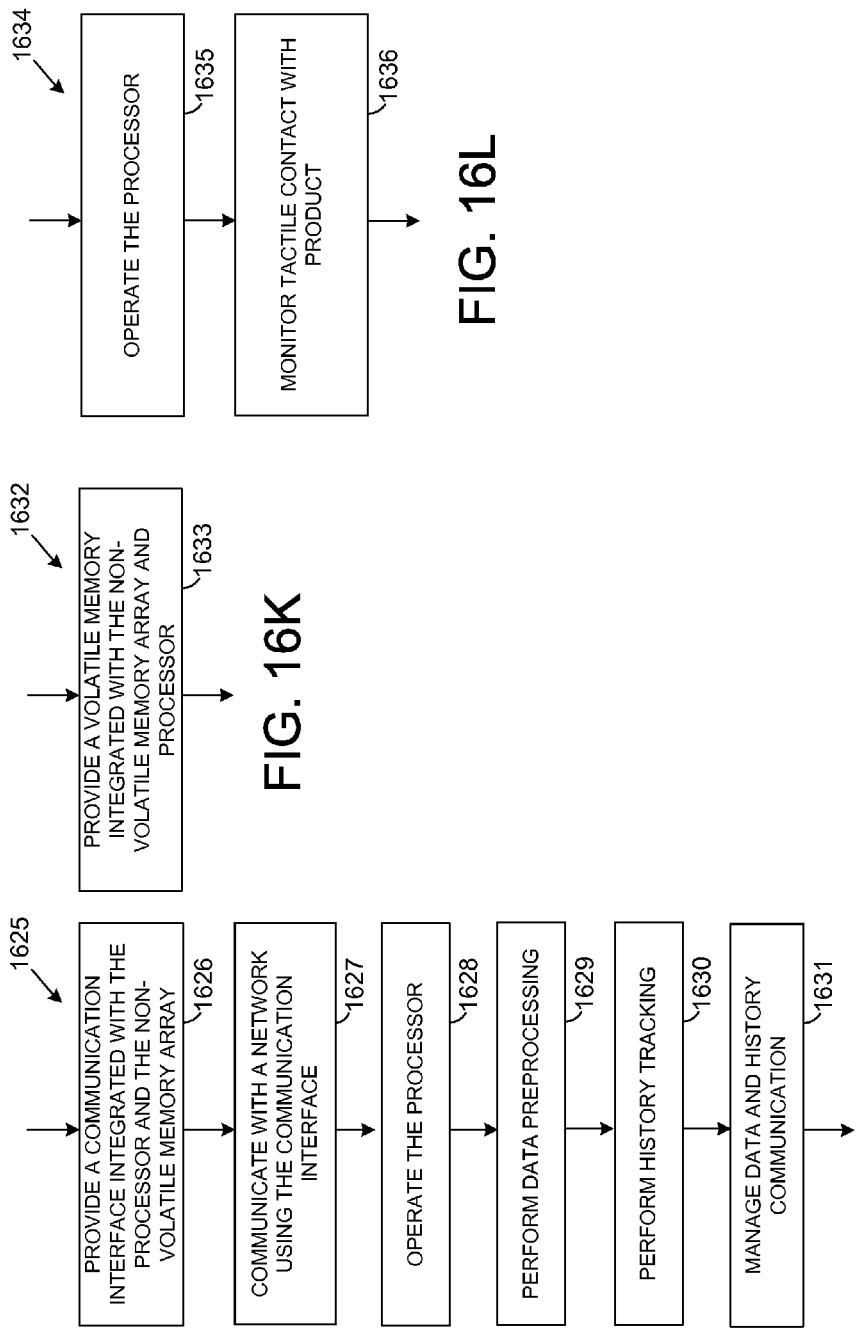

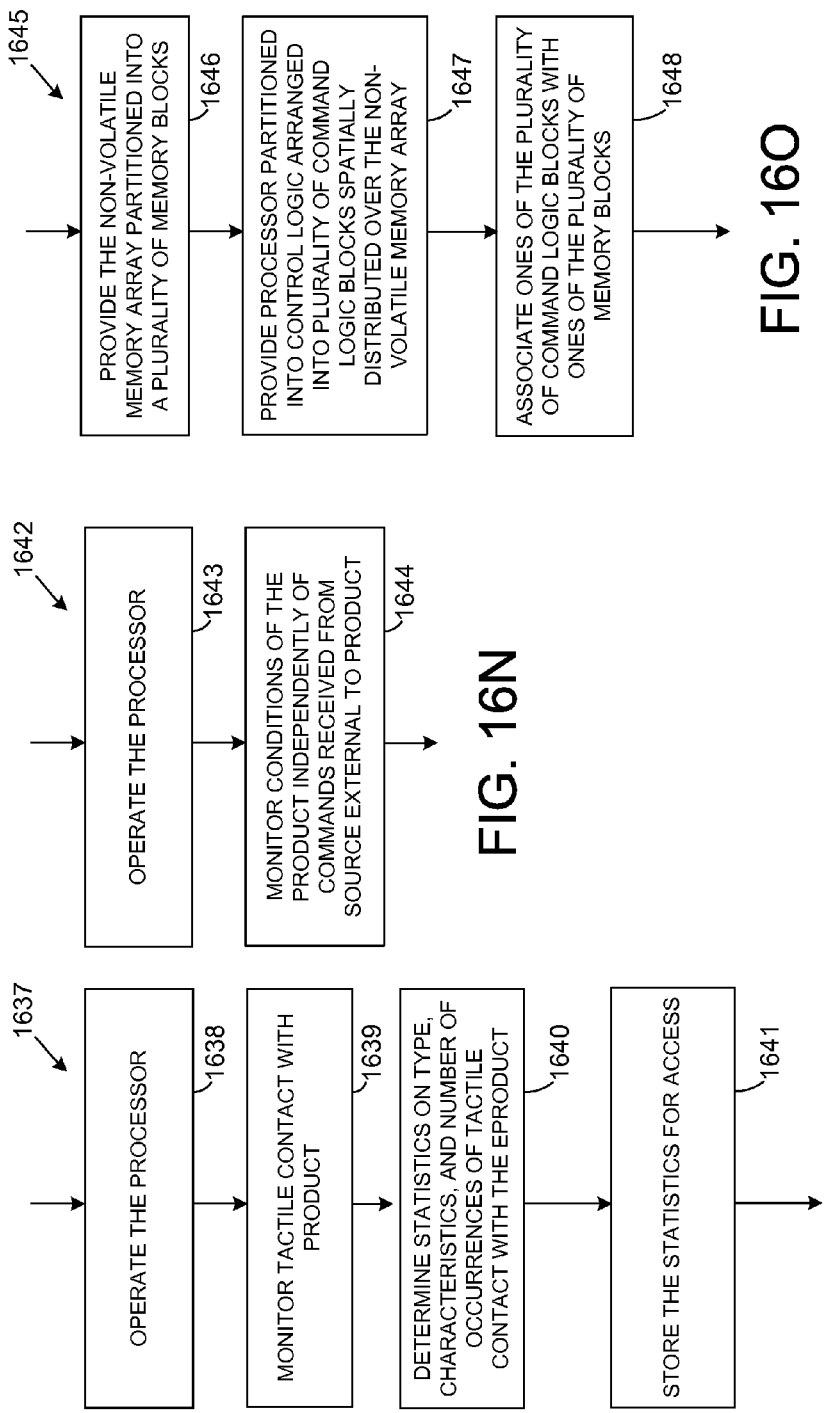

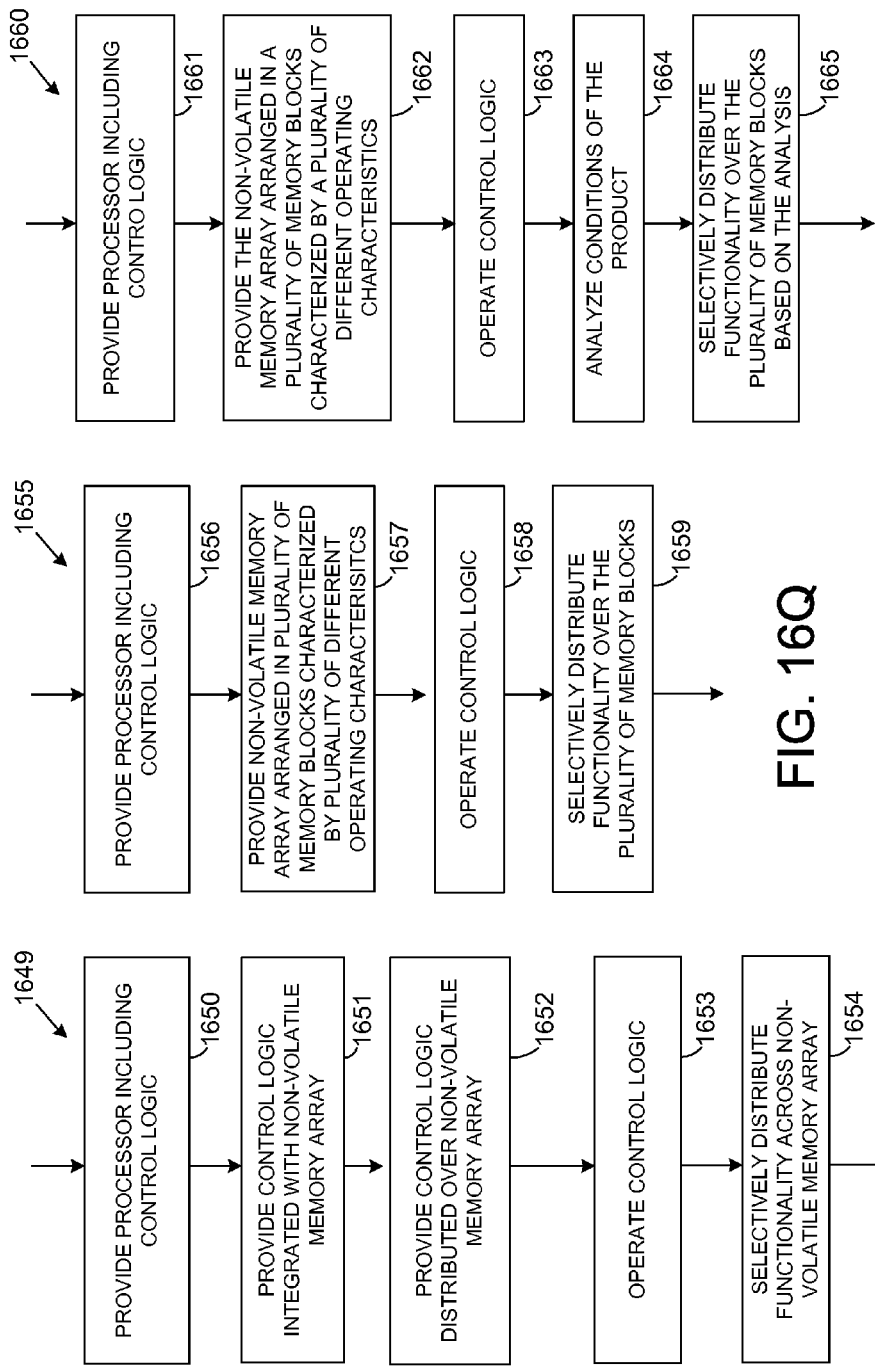

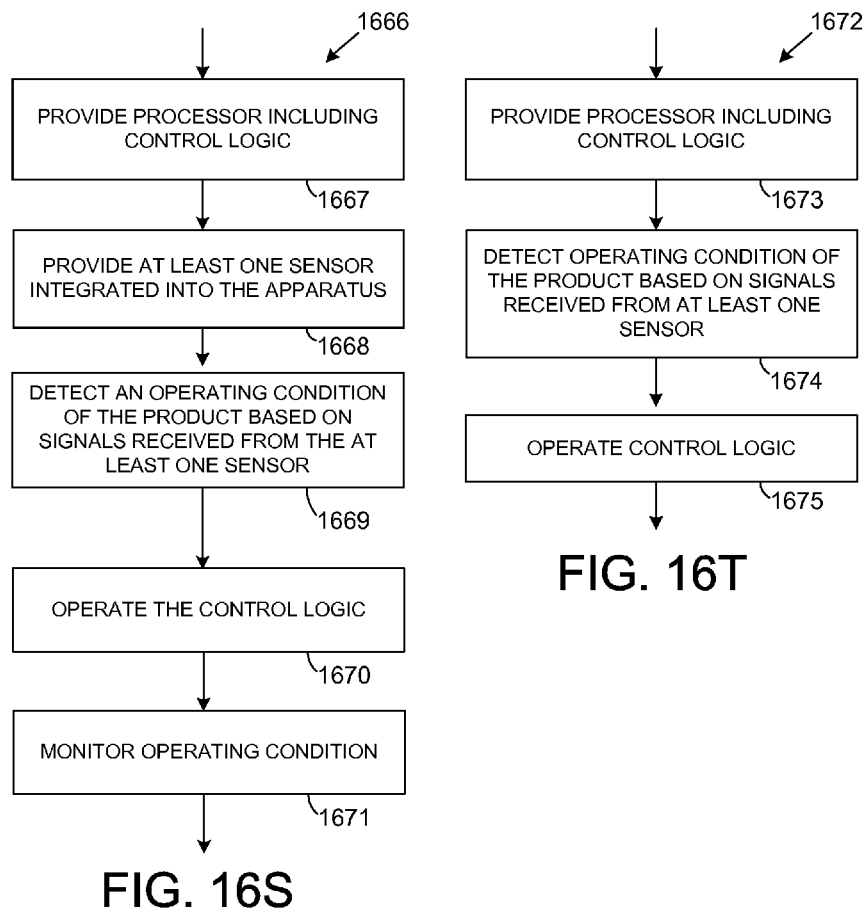

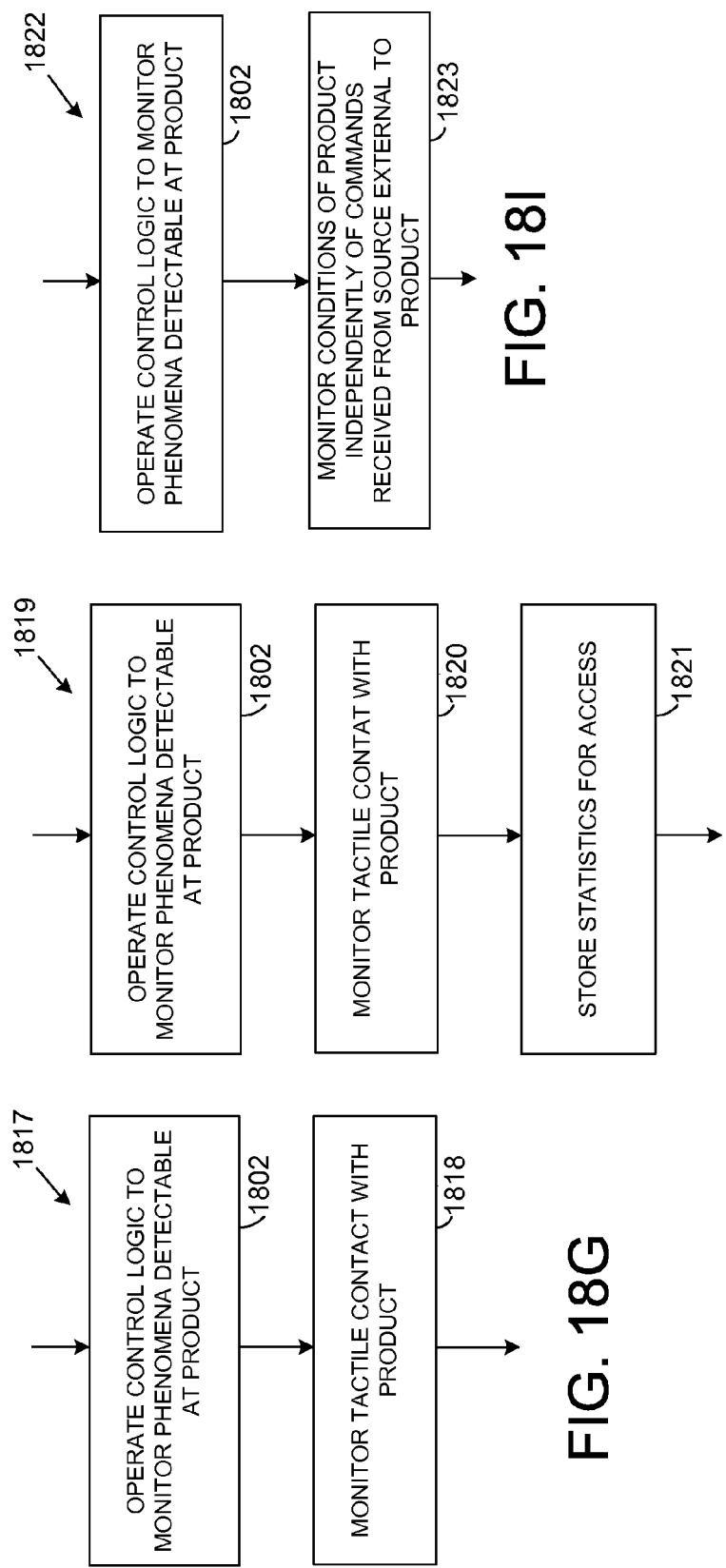

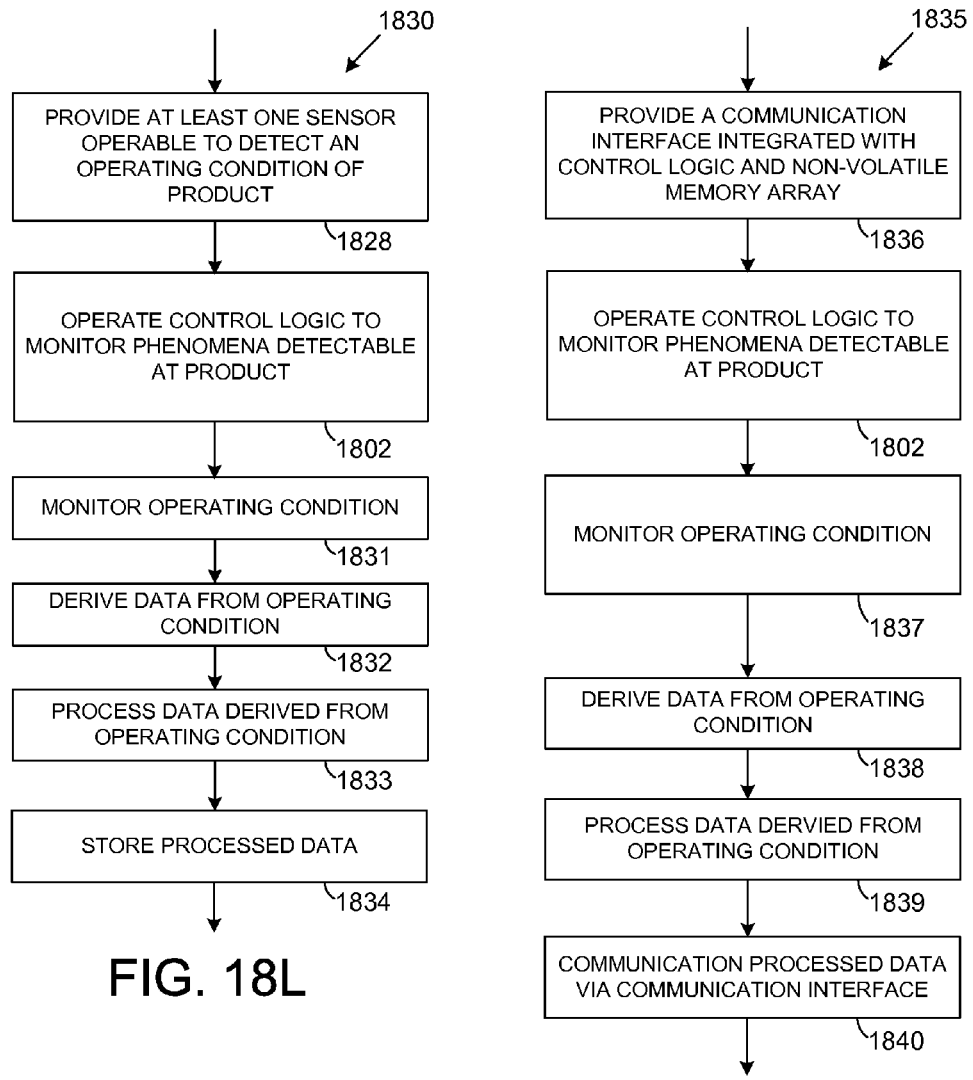

FLEXIBLE PROCESSORS AND FLEXIBLE MEMORY

CROSS-REFERENCE TO RELATED APPLICATIONS

The present application is related to and/or claims the benefit of the earliest available effective filing date(s) from the following listed application(s) (the "Priority Applications"), if any, listed below (e.g., claims earliest available priority dates for other than provisional patent applications or claims benefits under 35 USC §119(e) for provisional patent applications, for any and all parent, grandparent, great-grandparent, etc. applications of the Priority Application(s)). In addition, the present application is related to the "Related Applications," if any, listed below.

PRIORITY APPLICATIONS

For purposes of the USPTO extra-statutory requirements, the present application constitutes a continuation-in-part of U.S. patent application Ser. No. 13/678,430 entitled Intelligent Monitoring for Computation in Memory, naming Roderick Hyde, Nicholas Pasch, and Clarence T. Tegreene as inventors, filed 15 Nov. 2012, which is currently co-pending or is an application of which a currently co-pending application is entitled to the benefit of the filing date;

For purposes of the USPTO extra-statutory requirements, the present application constitutes a continuation-in-part of U.S. patent application Ser. No. 13/687,983 entitled Error Correction with Non-Volatile Memory on an Integrated Circuit, naming Roderick Hyde, Nicholas Pasch, and Clarence T. Tegreene as inventors, filed 28 Nov. 2012, which is currently co-pending or is an application of which a currently co-pending application is entitled to the benefit of the filing date; and For purposes of the USPTO extra-statutory requirements, the present application constitutes a continuation-in-part of U.S. patent application Ser. No. 13/678,439 entitled Redundancy for Loss-Tolerant Data in Non-Volatile Memory, naming Roderick Hyde, Nicholas Pasch, and Clarence T. Tegreene as inventors, filed 15 Nov. 2012, which is currently co-pending or is an application of which a currently co-pending application is entitled to the benefit of the filing date.

RELATED APPLICATIONS

None.

The United States Patent Office (USPTO) has published a notice to the effect that the USPTO's computer programs require that patent applicants reference both a serial number and indicate whether an application is a continuation, continuation-in-part, or divisional of a parent application. Stephen G. Kunin, Benefit of Prior-Filed application, USPTO Official Gazette Mar. 18, 2003. The USPTO further has provided forms for the Application Data Sheet which allow automatic loading of bibliographic data but which require identification of each application as a continuation, continuation-in-part, or divisional of a parent application. The present Applicant Entity (hereinafter "Applicant") has provided above a specific reference to the application(s) from which priority is being claimed as recited by statute. Applicant understands that the statute is unambiguous in its specific reference language and does not require either a serial number or any characterization, such as "continuation" or "continuation-in-part," for claiming priority to U.S. patent applications. Notwithstanding the foregoing, Applicant understands that the USPTO's computer programs have certain data entry requirements, and hence Applicant has provided designation(s) of a relationship between the present application and its parent application(s) as set forth above and in any ADS filed in this application, but expressly points out that such designation(s) are not to be construed in any way as any type of commentary and/or admission as to whether or not the present application contains any new matter in addition to the matter of its parent application(s).

If the listings of applications provided above are inconsistent with the listings provided via an ADS, it is the intent of the Applicant to claim priority to each application that appears in the Priority Applications section of the ADS and to each application that appears in the Priority Applications section of this application.

All subject matter of the Priority Applications and the Related Applications and of any and all parent, grandparent, great-grandparent, etc. applications of the Priority Applications and the Related Applications, including any priority claims, is incorporated herein by reference to the extent such subject matter is not inconsistent herewith.

TECHNICAL FIELD

The present disclosure relates to electronic memory and systems associated with electronic memory.

SUMMARY

In one aspect, an apparatus includes but is not limited to a non-volatile memory array and a processor integrated with the apparatus. The processor is operable to operate in combination with the non-volatile memory array to accumulate information associated with a product. In addition to the foregoing, other aspects are described in the claims, drawings, and text forming a part of the present disclosure.

In one aspect, an apparatus includes but is not limited to a non-volatile memory array integrated into a product and control logic integrated with and distributed over the non-volatile memory array. The control logic can be operable to monitor phenomena detectable at the product. In addition to the foregoing, other aspects are described in the claims, drawings, and text forming a part of the present disclosure.

In one aspect, a method of operating an apparatus includes but is not limited to providing a processor integrated with a non-volatile memory array and the apparatus, operating the processor in combination with the non-volatile memory array, and accumulating information associated with a product. In addition to the foregoing, other aspects are described in the claims, drawings, and text forming a part of the present disclosure.

In one aspect, a method of operating an apparatus includes but is not limited to providing a control logic integrated with and distributed over a non-volatile memory array and integrated into a product, and operating the control logic to monitor phenomena detectable at the product. In addition to the foregoing, other aspects are described in the claims, drawings, and text forming a part of the present disclosure.

In one aspect, an information handling system includes but is not limited to means for operating a processor integrated with a non-volatile memory array and an apparatus, and means for accumulating information associated with a product. In addition to the foregoing, other aspects are described in the claims, drawings, and text forming a part of the present disclosure.

In one aspect, a system includes but is not limited to circuitry for operating a control logic integrated with and distributed over a non-volatile memory array and integrated into a product, and circuitry for monitoring phenomena detectable at the product. In addition to the foregoing, other aspects are described in the claims, drawings, and text forming a part of the present disclosure.

BRIEF DESCRIPTION OF THE DRAWINGS

Embodiments of the invention relating to both structure and method of operation may best be understood by referring to the following description and accompanying drawings:

FIGS. 18A through 18M are multiple schematic flow charts showing several embodiments and/or aspects of a method of operating an apparatus including control logic integrated with memory and further integrated into a product.

DETAILED DESCRIPTION

Figure 1A:
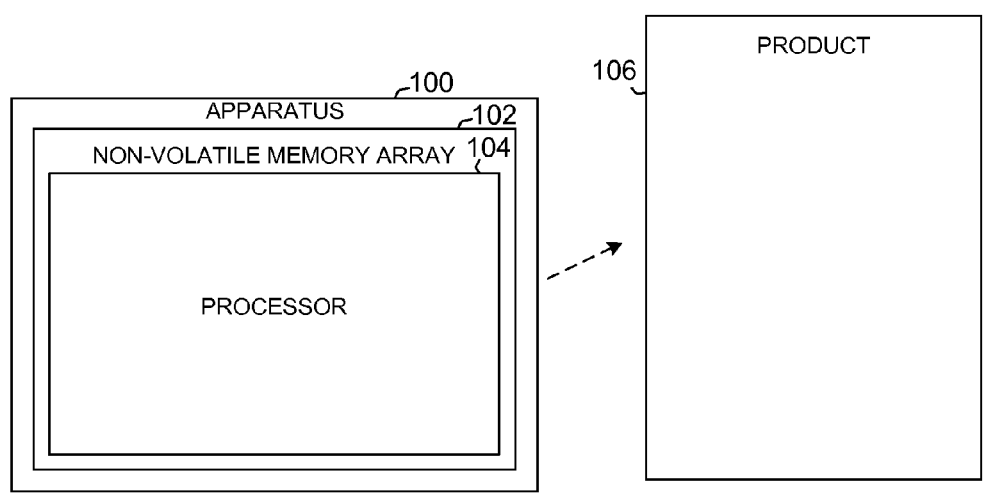
FIGS. 1A and 1B are schematic block diagrams depicting top and side views of embodiments of an apparatus including processor and flexible memory that can be integrated universally into a variety of products.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

While various aspects and embodiments have been disclosed herein, other aspects and embodiments will be apparent to those having ordinary skill in the art. The various aspects and embodiments disclosed herein are for purposes of illustration and are not intended to be limiting, with the true scope and spirit being indicated by the following claims.

The various memory systems and devices disclosed herein are expected to be useful in many applications and contexts, and are further anticipated to be particularly useful in cloud computing and mobile contexts. In some configurations, the disclosed memory systems and devices can be used in system-on-a-chip (SOC) applications as processing and memory are distributed in more and more locations and applications throughout our technologically advancing society. The various memory systems and devices can include non-volatile memory including flash memory and electrically erasable programmable read-only memory (EEPROM) for usage in many electronic devices, such as mobile and cell phones, notebook computers, personal digital assistants, medical devices, medical diagnostic systems, digital cameras, audio players, digital televisions, automotive and transportation engine control units, USB flash personal discs, and global positioning systems.

In various applications and contexts, memory systems can include non-volatile memory integrated with a processor or other control logic, and a bus or other communications interface. As non-volatile memories and integrated system continue to evolve, their role in overall systems continue to expand to include various aspects of computation that is facilitated, for example, by phase-change memory in which passage of current switches a memory material between two states, crystalline and amorphous, or additional states that further elevate storage capacity.

Figure 1B:
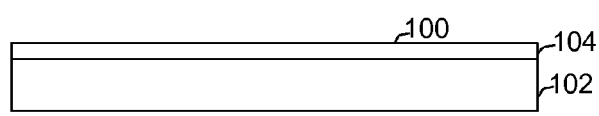

Referring to FIGS. 1A and 1B, schematic block diagrams depict top and side views of embodiments of an apparatus including processor and flexible memory that can be integrated universally into a variety of products. In an illustrative embodiment, an apparatus 100 including a non-volatile memory array 102 and a processor 104 integrated with the apparatus 100. The processor 104 is operable to operate in combination with the non-volatile memory array 102 to accumulate information associated with a product 106.

In some applications and/or embodiments, the processor 104 can be integrated with non-volatile memory array 102 to form the apparatus 100 which can be further integrated into the product 106, for example electronic devices, such as mobile and cell phones, notebook computers, personal digital assistants, medical devices, medical diagnostic systems, digital cameras, audio players, digital televisions, automotive and transportation engine control units, USB flash personal discs, and global positioning systems. Accordingly, the apparatus 100 can further include the product 106 integrated with the non-volatile memory array 102 and the processor 104.

In embodiments of the apparatus with processing capability of a processor or other control logic integrated in a distributed manner with non-volatile memory, the processing capability can be implemented with relatively low speed requirement to enable processors to be available in a ubiquitous manner. Accordingly, information can be acquired in a dispersed manner and intercommunicated over vast systems. Thus processors can be inexpensive and memory readily available for various consumer items. Custom versions of memory including non-volatile memory and RAM can be integrated into virtually any product, enabling widespread preprocessing in items such as door handles to determine who has accessed a location and how the access was made to allow any type of processing on the information.

In some embodiments, the apparatus 100 can be configured such that the processor 104 is operable to accumulate and communicate information about use of the product 106. For example, the apparatus can be used in various types of medical devices to monitor and store aspects of operation. In a particular example embodiment, the apparatus can be used in medical products to form biocompatible electronic products such as electronic devices or medical support materials that can dissolve in a patient's body. Some medical products can be configured to be biocompatible and encapsulated in a textile material, silk, or other suitable substrate that dissolves after a selected time duration. The apparatus can also be constituted in a biodegradable form for implantation including biodegradable circuit components including transistors, diodes, inductors and capacitors that can dissolve in water or in the body.

In another example embodiment, the apparatus can be integrated into a product such as a vehicle, specifically a rental vehicle. For a rental automobile, the apparatus can be configured to monitor use such as distance, speed, or forces acting upon the automobile to ascertain driving behavior of the driver.

A further example application for use of the apparatus can be electrodes for a medical device, such as a Transcutaneous Electrical Nerve Stimulation (TENS) device or any other suitable device. A typical TENS system uses silver electrodes mounted on a fabric or cloth substrate. The apparatus including processor and memory can be integrated into the electrode for monitoring delivery of therapeutic pulses but also to monitor body signals such as electrical signals such as for diagnostic purposes. TENS devices produce electric current to stimulate the nerves for therapeutic purposes at a controlled or modulated pulse width, frequency and intensity. In various embodiments, the apparatus integrated into TENS electrodes includes processing capability that can enable chronic monitoring of biological electrical signals to facilitate diagnostic monitoring as well as therapeutic control.

In further applications and/or embodiments, the apparatus 100 can be constructed with the processor 104 operable to accumulate and communicate information about at least one entity in association with the product 106. In various embodiments and/or applications, an entity can be a person, a living being, a non-living being, an organization (business, political, or otherwise), a device, a computer, a network, or the like. For purposes of example, the apparatus can be integrated into a biocompatible, biodegradable form for hemodynamic monitoring of pressure and blood flow within the circulatory system. Thus, the processor and integrated memory in the apparatus can enable Holter monitoring of an ambulatory patient independently of any external device, although supporting communication with a device external to the patient's body via telemetry for exchange of commands, instructions, control information, and data.

In still further embodiments, the apparatus 100 can be formed in which the processor 104 is operable to accumulate and communicate information about at least one entity in communication with the product 106. For example, the apparatus can be integrated into a weather monitoring device such as a thermometer, barometer, anemometer, multi-meter that measures multiple environmental parameters, or the like. The weather monitoring device can include an apparatus that includes a communication interface and sensors integrated with the processor and memory. The weather monitoring device can be in a relatively inaccessible location and can communicate from this location to an entity, such as a weather computer or a person.

In additional example embodiments or applications, the apparatus 100 can be implemented so that the processor 104 is operable to accumulate and communicate information about at least one entity in contact with the product 106. For example, the apparatus can be integrated with a product in the form of a patient armband in hospitals, identification armband in workplaces or other locations, and the like, for instance to assist in security operations. In another example, the apparatus can be integrated with a product in the form of a soda can or other packaging, for example to assist in automatic or effortless purchase of the product.

In various embodiments, the apparatus 100 can be configured such that the processor 104 is operable to monitor tactile contact with the product 106. In some applications and/or conditions, tactile contact can be monitored via a tactile sensor accessed by the apparatus that can either be integrated into the apparatus, or the processor can be configured to accept tactile information from a distal sensor. In other applications, tactile information can be sent to the apparatus and processor. In example configurations, the apparatus can be integrated into a product in the form of a steering wheel, joystick, or other control device, and the control logic and memory can be configured to perform precision control operations. In another example embodiment, the apparatus can be integrated into a product in the form of a sports article such as a football, and the control logic and memory can be constructed to detect and identify a person with control of the product, such as identifying who has recovered a fumble.

In a particular example embodiment, the apparatus 100 can be constructed with the processor 104 operable to monitor tactile contact with the product 106, determine statistics on type, characteristics, and number of occurrences of tactile contact with the product 106, and store the statistics for access. For example, the apparatus can be integrated into a product in the form of a door handle or door handle sleeve. The processor and memory can be configured to monitor conditions such as who, what, when, and how many people have touched the door handle or sleeve. Some embodiments can monitor how hard the door handle or door handle sleeve is touched.

In various embodiments, the apparatus 100 can include volatile memory (not shown) in combination with the non-volatile memory array 102. Accordingly, in further applications or contexts for embodiments, the apparatus 100 can further include a volatile memory integrated with the non-volatile memory array 102 and the processor 104.

In another example, the control logic can oversee operations of an overall system, maintaining statistics on the type and number of instructions communicated and processed. For example, future instructions and data can be predicted based on the determined statistics on type and number of instructions, and the predicted instructions and data can be compared to actually received instructions and data to detect unexpected conditions.

Figure 2A:
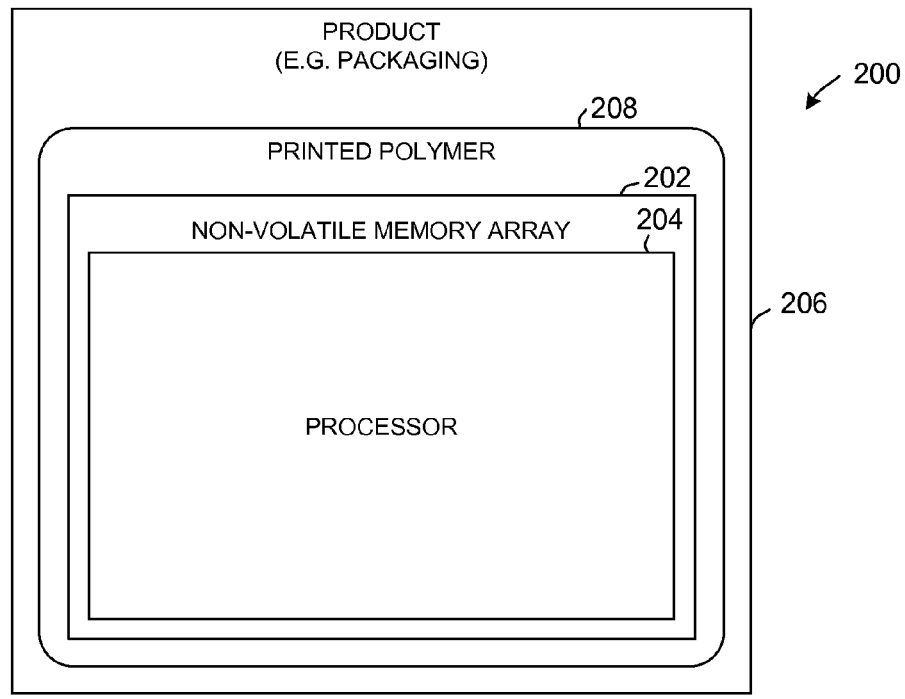
FIGS. 2A and 2B are respective top and side views of schematic block diagrams illustrating embodiments of an apparatus including processor and flexible memory that can be integrated on a printed polymer substrate universally into a multiple types of products.
Figure 2B:
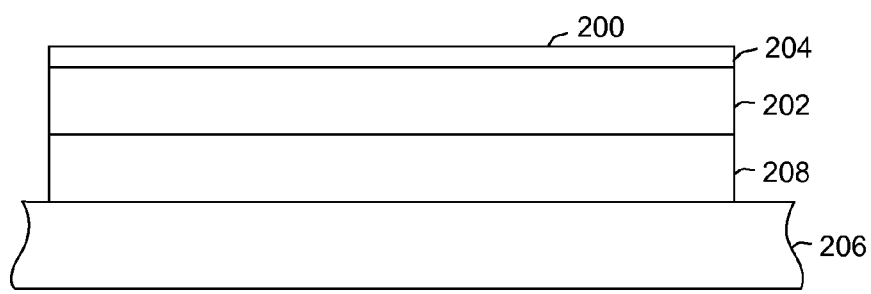

Referring to FIGS. 2A and 2B, respective top and side views of schematic block diagrams illustrate embodiments of an apparatus including processor and flexible memory that can be integrated on a printed polymer substrate universally into a multiple types of products. In particular embodiments, the apparatus 200 can be arranged in a manner that the processor 204 and the non-volatile memory array 202 are integrated onto a printed polymer 208 for integration with the product 206. In some applications and/or contexts, an apparatus can be formed of printed non-volatile memory on polymer. For example, the apparatus can be formed on a printed polymer integrated into packaging material and the integrated processor and memory can perform operations such as monitoring the number and type of touches of the product to determine marketing-relevant information such as attractiveness of the packaged material to consumers.

Figure 3A:
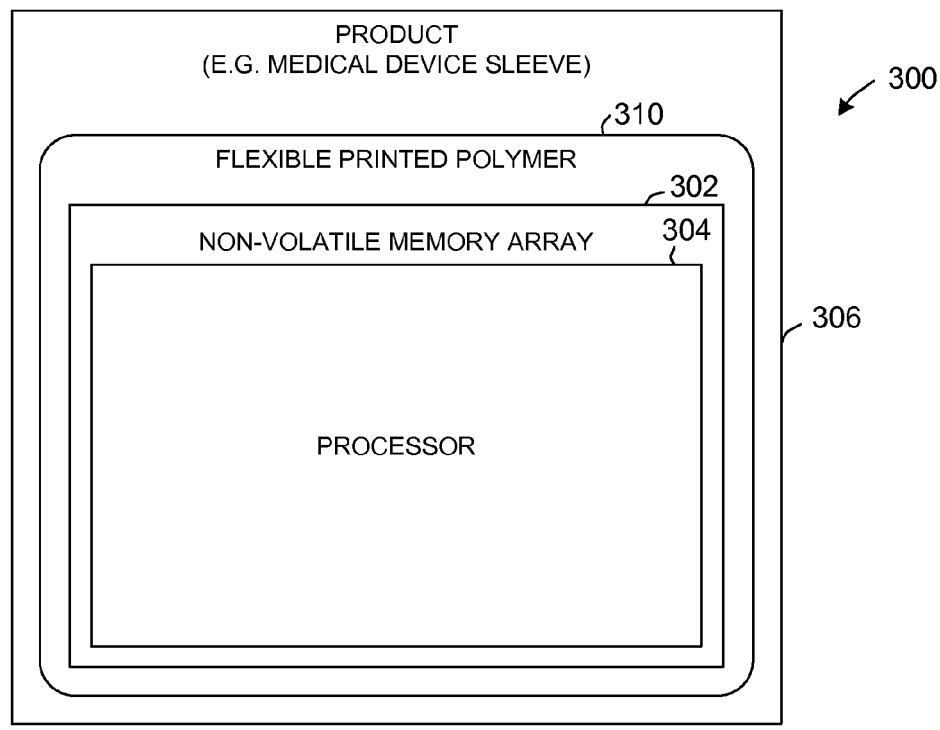
FIGS. 3A and 3B are respective top and side views of schematic block diagrams showing embodiments of a an apparatus including processor and flexible memory that can be integrated on a flexible printed polymer substrate universally into a multiple types of products.
Figure 3B:
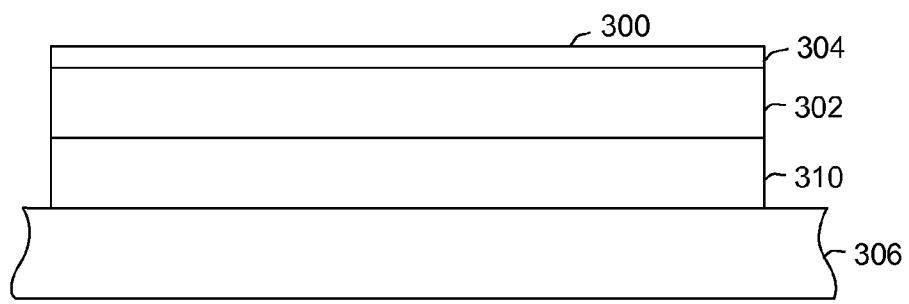

In some arrangements, a printed non-volatile memory on polymer can form flexible memories. In embodiments of the memory device depicted in FIGS. 3A and 3B, respective top and side views of schematic block diagrams show embodiments of a an apparatus including processor and flexible memory that can be integrated on a flexible printed polymer substrate universally into a multiple types of products. The apparatus 300 can be composed such that the processor 304 and the non-volatile memory array 302 are integrated onto a printed flexible polymer 310 for integration with the product 306. For example, the apparatus integrated onto a printed flexible polymer can be a product in the form of a medical device sleeve or patch, and the control logic and memory configured for use in monitoring implanted medical devices such as knee implants, hip implants, shoulder implants, elbow implants, and the like. The processor and memory can be configured to monitor aspects of performance such as position, angle, angular velocity or acceleration, other dynamics, and the like. In some arrangements, the processor and memory can be configured to assist physical therapy such as measurement of motion. In further arrangements, the processor and memory can be configured to monitor other biological or physiological functions such as blood flow, cardiac performance, hemodynamics, neurological aspects of action, and the like.

Accordingly, a flexible memory can be integrated with processors for further integration into any type of product, even very simple products such as bottles, cans, or packaging materials. A non-volatile memory can be integrated in a system of any suitable product such as, for example, a door handle sleeve to detect and record who, what, when, and how anyone has touched the door handle. Such a system can be used to facilitate access or to provide security. In other examples, a non-volatile memory and processor in some applications with sensors and/or a communication interface can be used in a flexible device for a medical product such as bandages or implants. These products can be formed of dissolvable materials for temporary usage, for example in biocompatible electronic or medical devices that can dissolve in a body environment, or environmental monitors and consumer electronics that can dissolve in compost. Other applications of products incorporating non-volatile memory and processor can include sporting equipment, tags such as for rental cars, patient armbands in hospitals tied to sensors, smart glasses, or any type of device.

In a particular example embodiment and application, the apparatus integrated as a printed flexible polymer can be used for cardiac monitoring such as in the form of a patch that can be attached to a patient's chest or elsewhere on the body. The processor and integrated memory can be used to control continuous monitoring of cardiac signals and activity. The apparatus can enable monitoring, such as by electrocardiography, independently of a separate medical device, although supporting communication and exchange of commands, instructions, and data with an external device.

In further embodiments, instead of a flexible polymer, the non-volatile memory and processor can be formed of silicon that is sufficiently thin to become flexible and thus formed as an inexpensive printed circuit component. Flexible memory in ubiquitous items, using polymer memory or silicon memory, can enable various profitable services, for example in conjunction with medical devices, security services, automotive products, and the like.

Figure 4A:
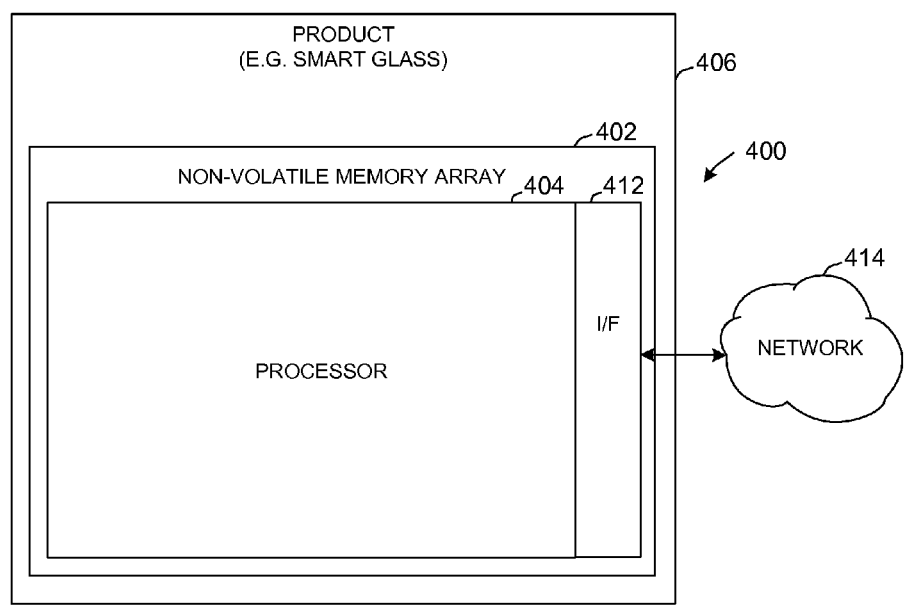
FIGS. 4A and 4B are schematic block diagrams illustrating respective top and side view of an embodiment of an apparatus including processor and flexible memory that can be integrated with a communication interface for communication with one or more devices external to the apparatus.
Figure 4B:
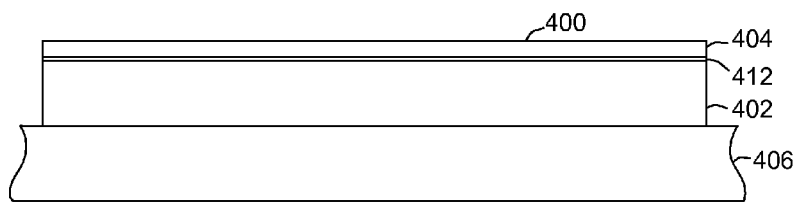

Referring to FIGS. 4A and 4B, schematic block diagrams illustrate respective top and side view of an embodiment of an apparatus including processor and flexible memory that can be integrated with a communication interface for communication with one or more devices external to the apparatus. Hence, the apparatus 400 can further include a communication interface 412 integrated with the processor 404 and the non-volatile memory array 402, the communication interface 412 operable for communication with a network 414.

In an example embodiment, the apparatus 400 can be integrated into a product 406 in the form of smart glass, magic glass, switchable glass, smart windows or switchable windows for application in windows or skylights, which is electrically switchable glass or glazing which changes light transmission properties when voltage is applied. The apparatus can use the integrated processor and memory to control the amount of light and thus heat transmission. The processor 404 can use the communication interface 412 to receive control commands, instructions, and data from a control center or operator, for example to activate the glass to change the glass between transparent and translucent, partially or fully blocking light while maintaining a clear view through the glass, if desired. In some embodiments, the communication interface 412 can be used to report on conditions associated with the window or skylight.

The apparatus can thus be used for a wide variety of data communication operations to enable concentration of data originating from many sources. In particular arrangements, a apparatus can include multiple types of memory with multiple memory characteristics in terms of cost, price, power, reliability, and the like. A apparatus can be optimized to any desired characteristic such as memory quality, memory power, cost in terms of number of electrons, noise, power consumption, and others. For example, power consumption can be optimized by lowering access threshold. The control logic can be configured to determine the source of noise, for example if noisy during writing, the control logic can determine how little write current can be used, thereby reducing power consumption. The control logic can be used to monitor electrical characteristics such as power or charge. Only so many electrons are available in a memory and the control logic can be configured to determine how few electrons can be used to perform a particular operation such as read/write operations.

In some embodiments, a apparatus can be operable to perform intelligent information handling using control logic that is distributed in memory and includes a bus for communication with devices external to the apparatus such as one or more processors.

The memory can be selected from a memory integrated circuit or memory chip, register, register file, random access memory (RAM), volatile memory, non-volatile memory, read-only memory, flash memory, ferroelectric RAM (F-RAM), magnetic storage device, disk, optical disk, and the like. In some arrangements, the memory can include multiple types of memory including the non-volatile memory array in the form of multiple types of non-volatile memory technologies, in addition to portions of memory that may be volatile. The memory may include multiple types of memory for use in a redundant fashion. Accordingly, the memory can include two or more memory segments of any non-volatile memory type or technology including read-only memory, flash memory, ferroelectric random access memory (F-RAM), magneto-resistive RAM (M-RAM) or the like. The processor or control logic can operate a segment of M-RAM which is comparable in speed and capacity to volatile RAM while enabling conservation of energy, rapid or instantaneous start-up and shutdown sequences. In other applications, the memory can include memory in the form of charge-coupled devices (CCDs) that are not directly addressable or other pure solid state memory that is reliable and inexpensive for use as separate memory for various applications such as cell phones, and the like.

Some types of memory can be susceptible to failure under specified conditions. For example, two-terminal non-volatile memory devices based on resistance switching effects, called memristors, are susceptible to damage from temperature and bias field conditions. Placing a memristor in an oven or applying a bias field can erase the entire memory. A memory can include a portion of memory which is susceptible to a particular condition and another, redundant portion for information handling operations which are resistant to the condition, thereby enabling operation in a RAID (redundant array of independent disk) array fashion to ensure retention of data during condition episodes. In case of accidental erasure, the processor or control logic can perform functionality analogous to that of a RAID array, for example, to use a slow memory that is impervious to magnetic fields to rebuild the erased data. In a particular embodiment, the slow memory can maintain hash tables are can be heat or magnetic-resistant. A two-way hash can be used to represent data as a hash, thereby reducing memory size.

For a memory that includes sufficiently large and inexpensive memory, the processor or control logic can perform a copy function at predetermined intervals, for example every 50 cycles or other selected rate, to copy the state to a redundant fast memory for copying to a slow memory, and to facilitate decision-making in memory. Thus, the memory can control sampling with the control logic including sampling functionality, and sampling of fast memory. For applications or contexts such as video handling in which only intermittent frames are sufficient to produce a suitable video image, a backup into lossy memory may be suitable to enable a basic recovery of data. In some embodiments, the memory may include excess memory in the form of flip-chip via a dedicated bus to send data from a first fast memory to a second fast memory.

In some embodiments and/or applications, the apparatus 400 can further include a communication interface 412 integrated with the processor 404 and the non-volatile memory array 402. The communication interface 412 can be operable for communication with a network 414. The processor 404 can be operable to perform data preprocessing, history tracking, and manage data and history communication. For example, the apparatus can be integrated into a window and include one or more sensors and communication interface in combination with the processor and memory. The sensor(s) can include a light sensor, a pressure sensor, and a temperature sensor for use in determining conditions that can be monitored and communicated to enable control of a heating and cooling system of a building.

Figure 5A:
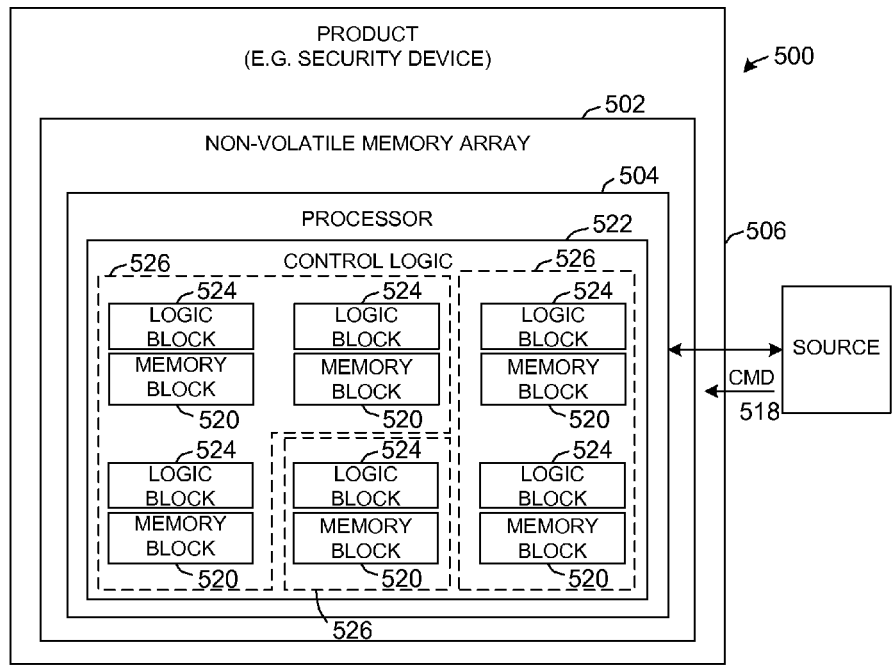
FIGS. 5A and 5B are schematic block diagrams showing respective top and side view of an embodiment of an apparatus including processor and flexible memory that is capable of autonomous operation independently of devices external to the apparatus.
Figure 5B:
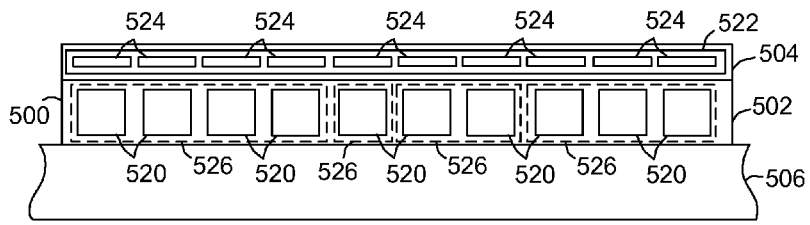

Referring to FIGS. 5A and 5B, schematic block diagrams show respective top and side view of an embodiment of an apparatus including processor and flexible memory that is capable of autonomous operation independently of devices external to the apparatus. Accordingly, the apparatus 500 can be configured with the processor 504 operable to monitor conditions of the product 506 independently of commands 518 received from a source external to the product 506. For example, the apparatus can be integrated to a product in the form of a security device for securing an item such as a home, an automobile, or any other item of value. The apparatus can monitor conditions of the product autonomously of devices external to the product, while supporting updates to the apparatus.

In some embodiments of the memory device depicted in FIGS. 5A and 5B, the apparatus 500 can be formed in which the non-volatile memory array 502 is partitioned into a plurality of memory blocks 520. The processor 504 can include control logic 522 partitioned into a plurality of command logic blocks 524 spatially distributed over the non-volatile memory array 502 with one or more of the plurality of command logic blocks 524 associated with ones of the plurality of memory blocks 520. Memory blocks can include a segment of memory, a memory portion, memory cells in a range of addresses either physical or virtual, a memory segment of a predetermined size, pages, memory entities of a predetermine size such as byte, word, defined-size word, fixed-size memory cells, and the like.

In some applications and/or embodiments, the apparatus can incorporate information processing in which a data copy can be compressed in a suitable manner. The control logic can perform operations relatively slowly, avoiding the heat buildup that can result from a fast data transfer. Thus, redundant backup memory buses can be run at comparatively slow speed, thereby avoiding a significant increase in the heat budget for information processing.

In various applications, the apparatus can facilitate operations by virtue of a large distributed area of processing or logic which can be spread over a relatively large area of memory storage. In some embodiments, the processor can be formed of logic that is relatively low capability or relatively low quality, for example to enable a small number of relatively simple operations, thereby reducing the number of layers of silicon in the integrated circuit chip, and possibly reducing power requirements and heat dissipation. The processing logic of such a processor-in-memory (PIM) can be widely distributed over the area of memory storage. The intelligent monitoring apparatus can be formed as at least part of a system-on-a-chip (SOC).

In some embodiments, the apparatus 500 can be arranged in a manner that the processor 504 includes control logic 522 integrated with and distributed over the non-volatile memory array 502. The control logic 522 can be operable to selectively distribute functionality across the non-volatile memory array 502.

In some constructions, the apparatus can include control logic formed in a limited number of metal layers within the memory logic. To avoid stacking of multiple layers of silicon processing on the memory chip, the control logic can be spread laterally across the memory array circuitry. Limited complexity of operations implemented on the apparatus circuit enables slower computation speed in comparison to a typical central processing unit (CPU). Such slower computation speeds are suitable since the limiting factor in transfers of data from a processor to memory is the data bus.

The control logic can be configured to reduce the percentage of transistor underutilization, called "dark silicon", by breaking up of the command structure of central blocks. The control logic can be further configured to enhance efficiency by performing background operations such as sorting of data within the memory while the system is idle.

In various embodiments, the apparatus 500 can be implemented so that the non-volatile memory array 502 includes a plurality of memory blocks 520 characterized by a plurality of different operating characteristics 526. The processor 504 can include control logic 522 operable to selectively distribute functionality over the plurality of memory blocks 520.

Different types of memory can have different operating characteristics. The apparatus can be formed of multiple memory segments that have different operating characteristics, for example in aspects of speed, power consumption, size, as well as susceptibility or resistance to particular operating conditions such as magnetic field characteristics, temperature, gravity, humidity, moisture, vibration, pressure, sound, electrical fields or conditions such as voltage, current, power, resistance, and other physical aspects of the environment. The control logic can operate as a memory controller integrated with the non-volatile memory array to allocate redundant storage for information handling taking into consideration memory type. In some applications, the control logic can optimize for the particular memory type depending, for example, on application constraints such as the amount of computation, energy consumption load, and many other conditions. For example, control logic metadata can supplies intra-memory hints about heat generation. Application constraints based on monitoring can include accuracy, amount of computation, response rate, energy consumption load, ease of calibration, programming, monitoring of continuous or discrete levels, and the like.

For example, in some embodiments, the apparatus can include both phase change memory (PCRAM) and other memory types and the control logic can assign memory usage according to various operating characteristics such as available power. In a specific example, PCRAM and DRAM may be selected based on power considerations. PCRAM access latencies are typically in the range of tens of nanoseconds, but remain several times slower than DRAM. PCRAM writes use energy-intensive current injection, causing thermal stress within a storage cell that degrades current-injection contacts and limits endurance to hundreds of millions of writes per cell. In an apparatus that uses both PCRAM and DRAM, the control logic can allocate memory usage according to the write density of an application.

In an apparatus that includes multiple different types of memory including a spin-transfer M-RAM, the control logic can assign functionality at least in part based on the magnetic properties of memory. In a system that includes at least one portion of F-RAM, the control logic can exploit operating characteristics of extremely high endurance, very low power consumption (since F-RAM does not require a charge pump like other non-volatile memories), single-cycle write speeds, and gamma radiation tolerance. The apparatus can include different segments of different types of memory including volatile and non-volatile memory, flash, dynamic RAM (DRAM) and the like, and use the control logic to attain different performance/cost benefits.

In an example arrangement, the apparatus can include memory of two types, such as non-volatile RAM (NVRAM) and DRAM in combination with control logic that allocates memory accesses for the NVRAM. The control logic prevents frequent reuse of memory locations and stores frequently-changing metadata in DRAM. The control logic can also add checksums to detect and correct corruption.

In embodiments adapted to promote write durability, the apparatus can include a non-volatile memory array with multiple types of memory including at least one portion of memory characterized by elevated write endurance. In a particular embodiment, the non-volatile memory array can include at least on portion formed of M-RAM which is based on a tunneling magneto-resistive (TMR) effect. The individual M-RAM memory cells include a magnetic tunnel junction (MTJ) which can be a metal-insulator-metal structure with ferromagnetic electrodes. A small bias voltage applied between the electrode causes a tunnel current to flow. The MTJ is exposed to an external magnetic field and forms a hysteresis loop with two stable states, corresponding to 0 and 1 data states at zero magnetic field. M-RAM is characterized among non-volatile memory technologies as having excellent write endurance with essentially no significant degradation in magneto-resistance or tunnel junction resistance through millions of write cycles. Accordingly, the control logic can monitor and determine whether a particular application or process is characterized by frequent, enduring write operations and assign a portion of M-RAM to handle memory accesses.

Another memory technology characterized by write endurance is ferroelectric RAM (FeRAM). FeRAM can be constructed using material such as lead-zirconate-titanate (PZT), strontium-bismuth-tantalate (SBT), lanthanum substituted bismuth-tantalate (BLT), and others. An externally applied electric field causes polarization of the FeRAM material to be switched and information retained even upon removal of the field. In absence of the electric field, polarization has two distinct stable states to enable usage in memory storage. FeRAM can have write endurance at the level of M-RAM and is further characterized by a reduced cell size and thus higher density. Thus, the control logic can monitor and determine whether a particular application or process is characterized by frequent, enduring write operations in combination with a relatively large number of storage cells. The control logic can assign a portion of FeRAM to handle memory accesses.

In certain applications and/or embodiments, the apparatus 500 can be configured such that the non-volatile memory array 502 includes a plurality of memory blocks 520 characterized by a plurality of different operating characteristics 526. The processor 504 can include control logic 522 operable to analyze conditions of the product 506 and selectively distribute functionality over the plurality of memory blocks 520 based on the analysis.

The apparatus can be configured with control logic with an abbreviated set of specific, basic functions in which simple operations can be off-loaded from a processor external to the apparatus and moved onto the apparatus. For example, context request blocks can be removed from the processor into the apparatus, for example for security purposes since the context request blocks are typically not located in the memory.

Embodiments of the apparatus with a reduced-functionality control logic can facilitate efficient operation of the apparatus while maintaining the integrated circuit simplicity and yield of the apparatus. Typically, the number of metal layers in a memory integrated circuit is substantially smaller than that of a processor circuit. Reducing the complexity of the control logic can allow fabrication with fewer metal layers.

In various embodiments, functionality control logic can be attained by one or more of several techniques. For example, computations can be simplified by implementing relatively simple tasks in the control logic or by acknowledging that a particular section of the memory is predominantly subject to a limited number of simple operations which can be implemented in the control logic while other operations that rarely are applied to the memory section can be performed by processing external to the apparatus. In another example, for operations or applications characterized by a limited or coarse accuracy, such as relatively low-grade video signals, processing can be based on estimation. In a further example, the control logic can include support for multiple functions in which circuitry for the different functions can be spread over a distributed area of the non-volatile memory array, forming a large distributed area of simple processing functionality.

The control logic can be a processor, a distributed-circuitry processor, a processing unit, a processing unit distributed over memory, arithmetic logic and associated registers, a microprocessor, a graphics processing unit, a physics processing unit, a signal processor, a network processor, a front-end processor, a state machine, a coprocessor, a floating point unit, a data processor, a word processor, and the like.

For example, the control logic can access, if available, background information about data characteristics and applications to tailor the memory to the currently-executing application. In some embodiments, the memory device can include control logic that is configured to monitor current patterns in the memory and analyze using entropy laws, for example by determining the fluctuations in data using statistical mechanics techniques. The control logic can monitor memory accesses and determine the relative probability that the entropy of the data is currently outside an equilibrium level and so the data is expected to be characterized by increases or decreases over time. The entropy of an isolated system is expected to increase until reaching equilibrium.

In various embodiments, the apparatus can include a non-volatile memory array which includes one or more suitable memory technology. For example, memory technologies in the apparatus can include embedded flash, read-only memory (ROM), electrical fuse (one-time programmable), CMOS floating gate (multiple time programmable), CMOS floating gate (one-time programmable), and anti-fuse (one-time programmable). The different memory technologies can have various advantages and disadvantages for particular operations or applications. Some memory technologies can have relatively high density such as ROM and antifuse, while others have low density (for example electrical fuse and CMOS floating gate). Some technologies have good endurance such as embedded flash, and CMOS floating gate, while others have poor endurance, for example ROM, electrical fuse, CMOS floating gate, and antifuse. Various technologies can have different standby and active current including high current (electrical fuse), medium current (embedded flash and CMOS floating gate), and low current (ROM and antifuse). The memory technologies vary in random access time including fast (ROM and antifuse), medium (embedded flash and CMOS floating gate), and slow (electrical fuse). The memory technologies vary in security including high security (antifuse), medium security (embedded flash and CMOS floating gate), and slow security (ROM and electrical fuse). The memory technologies vary in high and low temperature and voltage tolerance including high tolerance (ROM and antifuse), medium tolerance (electrical fuse), and low tolerance (embedded flash and CMOS floating gate). In a apparatus that includes multiple memory sections with more than one memory technology, the control logic can monitor a history and pattern of memory accesses and assign memory usage depending on the monitoring. For data or code that changes very frequently, the control logic can assign embedded flash. For high volume storage, the control logic can assign more dense memory technologies. For applications in which the code changes infrequently, the control logic can allocate, for example, ROM and antifuse. The control logic can assign memory accesses depending on temperature and voltage conditions that can be measured using sensors or otherwise communicated to the apparatus. The control logic can determine the security level of an application and assign the memory technology accordingly.

In some applications and/or embodiments, different memory blocks can be allocated for respective different functionality so that the command logic blocks can support functionality that is specific to the appropriate memory blocks. For example, in some embodiments or applications a capability for the memory device to efficiently support memory blocks in which either or both bit maps and vector graphics may be useful. Accordingly, the memory device can be configured so that the memory includes a portion that is bit-mapped and a portion that is vector memory. For example, part of the memory can be optimized for pictures and video (JPEG) and another portion optimized for more computational applications. An example of such that context that would benefit from both memory types is a mobile telephone with camera and/or video functionality.

The apparatus can, in addition to including multiple types of memory, can include multiple different classes of memory of the same memory type to attain a desired operating characteristic. The different classes of memory may include memory of the same technology with different operating parameters or different fabrication process parameters. The different classes of memory may be formed with different polysilicon types, different metal types, different silicides or salicides, various source, gate, and spacer dimensions, different annealing processes, and any other suitable variation in fabrication technique.

In various conditions, applications, and/or embodiments, the apparatus can be configured to allocate different portions of memory that have differing characteristics to specific applications. Some characteristics of memory can be better for some applications. For example, the control logic can assign data in high-speed operations to high-speed memory while assigning less time-critical applications to slower memory. The control logic can take into consideration memory speed when allocating redundant memory sections, for example maintaining sampled data from high-speed operations in relatively slow-speed memory. The control logic can assign frequently updated information to memory types that are more durable to writes. In another example application, the apparatus can be used in an end-to-end image storage system which includes multiple types of memory including multiple types of non-volatile RAM. For example, the apparatus can be used to supply inexpensive memory such as memory stripes that are not part of a device such as a picture telephone, but is used to accumulate data (such as pictures) using some mirror communications that are facilitated by intelligence supplied by the control logic. In an example application, the control logic can activate to perform data communication when the apparatus is in a location sufficiently proximal to the picture telephone to enable data transfer. The control logic can be used to detect that the picture telephone and the apparatus are sufficiently close to perform a data transfer and, if so, operate in a low operation, low power mode to perform the data communication. Accordingly, the intelligence of the control logic can enable data transmission when the memory is in any location that is sufficiently close to the data source.

Figure 6A:
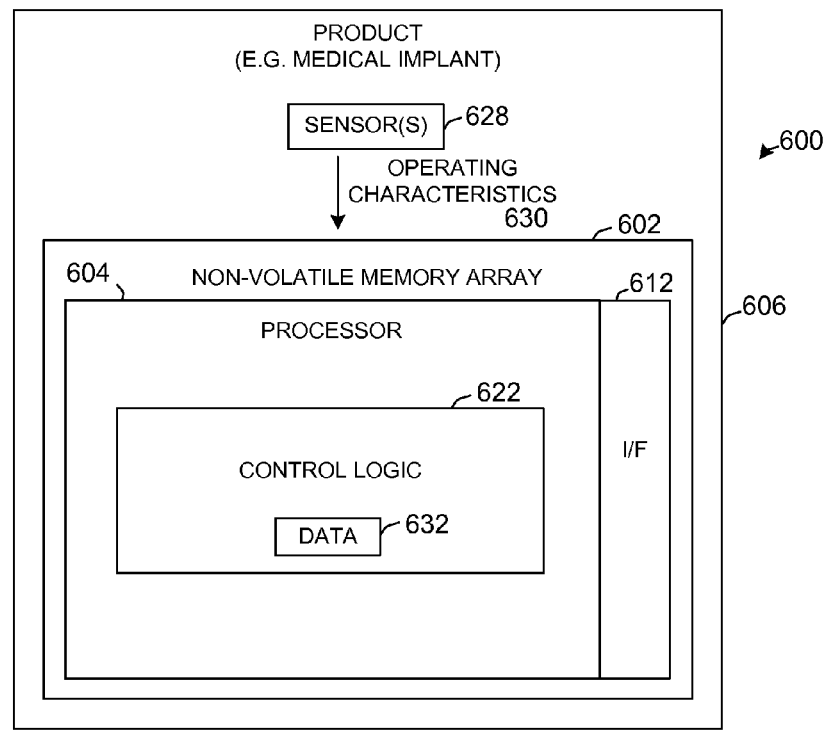
FIGS. 6A and 6B are respective top and side views of schematic block diagrams illustrating embodiments of an apparatus including processor and flexible memory that is capable of operating in combination with one or more sensors integrated with the apparatus to detect and react to operating conditions.
Figure 6B:
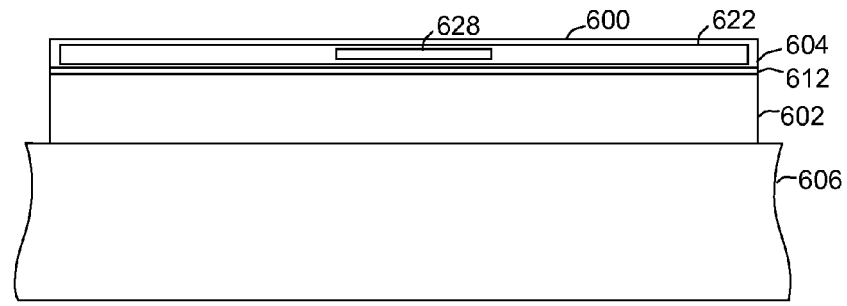

Referring to FIGS. 6A and 6B, respective top and side views of schematic block diagrams illustrate embodiments of an apparatus including processor and flexible memory that is capable of operating in combination with one or more sensors integrated with the apparatus to detect and react to operating conditions. For example, the apparatus can be integrated into a product in the form of a medical implant such as an orthopedic implant (knee, hip, shoulder, elbow, and the like), a cardiology implant such as a pacemaker, anti-tachycardia device, defibrillator, and the like. The apparatus can include any suitable type of sensor such as motion or position sensors, electrical signal sensors, pressure sensors, oxygen sensors, and the like. The processor and memory can be configured to facilitate monitoring for therapeutic and diagnostic purposes, and delivery of therapy.

Figure 7A:
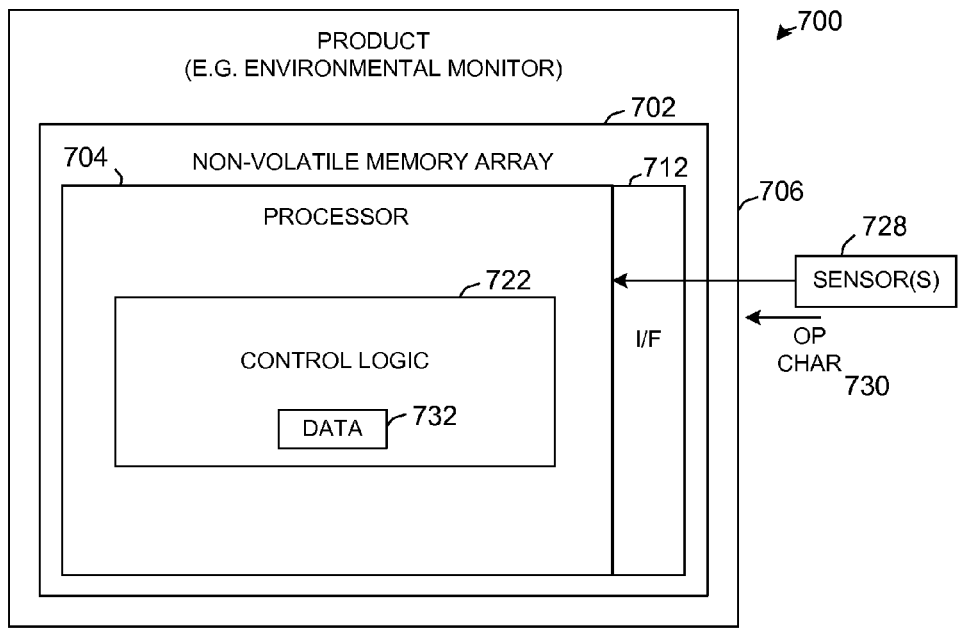
FIGS. 7A and 7B are respective top and side views of schematic block diagrams showing embodiments of an apparatus including processor and flexible memory that is capable of operating in combination with one or more sensors external to the apparatus to detect and react to operating conditions.
Figure 7B:
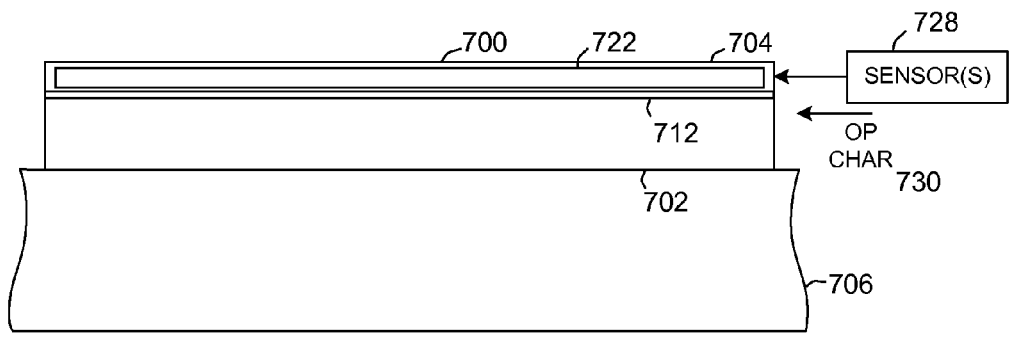

Referring to FIGS. 7A and 7B, respective top and side views of schematic block diagrams show embodiments of an apparatus including processor and flexible memory that is capable of operating in combination with one or more sensors external to the apparatus to detect and react to operating conditions. For example, the apparatus can be integrated with a product in the form of an environmental monitor such as for usage in environmental-critical applications such as computer and network data centers, hospitals, and museums. The apparatus can include any suitable type of environment sensor such as thermometers, pressure sensors, magnetic field sensors, moisture sensors, and the like. The environmental monitor can be used to monitor and maintain the environment within selected limits.

Referring to FIGS. 6A, 6B, 7A, and 7B, schematic block diagrams depict respective top and side view of an embodiment of an. Accordingly, the apparatus 600, 700 can further include at least one sensor 628, 728 operable to detect an operating condition 630, 730 of the product 606, 706. The processor 604, 704 can include control logic 622, 722 operable to monitor the operating condition 630, 730.

Thus, the control logic can be operable to perform maintenance operations including information handling in the memory in response to physical phenomena imposes on the memory. For example, the memory device can incorporate sensors or other components that detect phenomena which can be monitored by the control logic to detect magnetic fields, temperature, velocity, rotation, acceleration, inclination, gravity, humidity, moisture, vibration, pressure, sound, electrical fields or conditions such as voltage, current, power, resistance, and other physical aspects of the environment to enable the control logic to perform actions to maintain, repair, clean, or other operations applied to the memory.

In some embodiments and/or applications, the apparatus 600, 700 can further include at least one sensor 628, 728 operable to detect an operating condition 630, 730 of the product 606, 706. The processor 604, 704 can include control logic 622, 722 operable to monitor the operating condition 630, 730, derive data 632, 732 from the operating condition 630, 730, process data 632, 732 derived from the operating condition 630, 730, and store the processed data 632, 732.

The memory device can include any suitable sensor for detecting a condition that may be useful for allocate memory usage. Example sensors can measure voltage, current, capacitance, resistance, inductance, capacitive/resistive, and other electrical or magnetic phenomena. Other suitable sensors can sense touch, tactile phenomena, pressure, vibration, velocity, acceleration, rotation, angular acceleration, angular velocity, and the like. Some sensors can sense ionic potential, optical radiation, electrochemical potential, infrared radiation, temperature, ionizing radiation, moisture, and the like.

In an embodiment of a memory device that includes multiple memory types or technologies, the sensor can detect electrical characteristics such as voltage or current and the control logic can determine whether the energy drive is sufficient to drive the memory reliably. If the energy drive is insufficient for a particular type of memory, the control logic can shift memory accesses to a memory type that can be reliably driven.

In some embodiments, a memory device can be configured to allocate memory for a particular application or operation based on scalability, for example by determining whether a substantial number of storage cells is to be used. For example, the memory device can be formed to store a redundant memory section for error detection and/or error correction in a decreased feature size to reduced overall storage footprint. PCRAM can be a highly scalable memory technology since thermal resistivity increases, contact area decreases, and the volume of phase-change material to block current flow decreases with feature size. As feature size becomes smaller, contact area decreases quadratically, and reduced contact area causes resistivity to increase linearly, causing programming current to decrease linearly. Thus PCRAM can attain not only smaller storage elements but also smaller access devices for current injection, leading to lower memory subsystem energy. Thus, the control logic can allocate PCRAM segments to applications characterized by large memory use and density.

In various embodiments, the apparatus 600, 700 can further include a communication interface 612, 712 integrated with the processor 604, 704 and the non-volatile memory array 602, 702 and at least one sensor 628, 728 operable to detect an operating condition 630, 730 of the product 606, 706. The processor 604, 704 can include control logic 622, 722 operable to monitor the operating condition 630, 730, derive data 632, 732 from the operating condition 630, 730, process data 632, 732 derived from the operating condition 630, 730, and communicate the processed data 632, 732 via the communication interface 612, 712.

An operation at bootstrap loading can cause the system to report on the operating condition of all components (including all chunks of memory) to enable allocation of functionality based on performance of the components. The report can be any compilation, combination, arrangement, or expression of selected information and/or signals relating to the operating condition.

In a particular application, the memory device can include control logic that restores a persistent application state by mapping non-volatile memory pages across system reboot operations, for example by mapping non-volatile RAM pages in different processes including processes that are not necessarily concurrent. The control logic can also support access control in portions of the non-volatile RAM in the manner of file system access control.

In some applications, what is desired is a capability to store large amounts of data while allowing some amount of inaccuracy or error. Such an application can be video streaming. The memory device can thus be formed with at least a portion of the memory that is very inexpensive but lossy.

In a particular application, the apparatus can include control logic configured to predict different possible outcomes, for example predicting several possible outcomes and preparing for each, then use sensors, measurements, and monitoring to determine which outcome to activate at a particular time. Expected outcomes can be defined as the predicted behavior of the memory under the operating conditions, for example in terms of failure, error detection, and error correction. In some embodiments, the analysis can be a probability analysis taking into consideration the operating conditions.

Figure 8A:
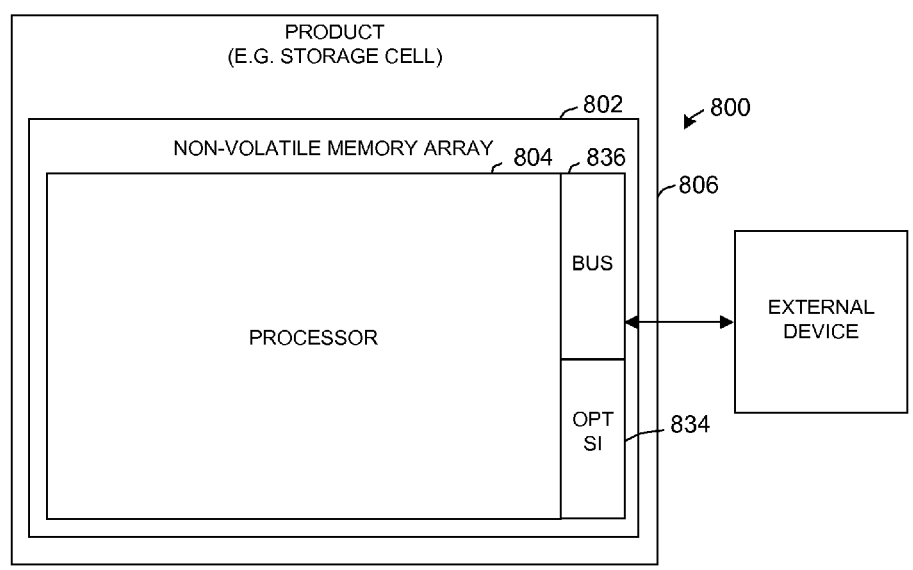
FIGS. 8A and 8B are schematic block diagrams depicting respective top and side view of an embodiment of an apparatus including processor and flexible memory and optical silicon that enables communication independent of a bus structure.
Figure 8B:
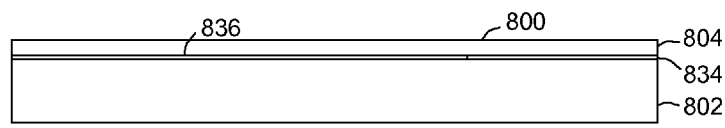

Referring to FIGS. 8A and 8B, schematic block diagrams depict respective top and side view of an embodiment of an apparatus including processor and flexible memory and optical silicon that enables communication independent of a bus structure. Thus, the apparatus 800 can further include optical silicon 834 operable to communicate optically, independently of a bus structure 836 coupled to the apparatus 800. The processor 804 can be operable to operate in combination with the non-volatile memory array 802 to accumulate information about the product 806 using the optical silicon 834 independently of communication on the bus structure 836. In an example application, the apparatus can be integrated into a product in the form of storage cells, such as with an individual apparatus allocated to individual storage cells. The processor and integrated memory can be configured to use the optical silicon to intercommunicate among cells to assist in monitoring which cells are occupied and what item is occupying the cells.

For example, the apparatus 800 can further include optical silicon 834 operable to communicate optically, independently of a bus structure 836 coupled to the apparatus 800. The processor 804 can be operable to operate in combination with the non-volatile memory array 802 to receive instructions for controlling accumulation of information about the product 806 using the optical silicon 834 independently of communication on the bus structure 836. The optical silicon can enable data to pass more quickly from outside the memory device to the memory. The memory device can support a WiFi network which optimizes memory for a particular application. Optical silicon can be used to alleviate some of the bandwidth problem for reading high volumes of data, such as for moving photographs from a camera or camera-phone to a storage device such as a computer or library. The bus can manage error detection and/or error correction by writing a copy of data via the optical link to a redundant memory for error detection and/or error correction in a manner that does not interfere with the data path formed by the bus.

The apparatus can facilitate communication and handle additional bandwidth via usage of control logic that can predict subsequent transfers and write to memory accordingly to enable processing on the predicted data values. In some embodiments, the apparatus can include communication channels in addition to the bus to facilitate transfer of information for various management functions, alleviating the traffic on the bus. The bus structure can be any subsystem that transfers data between components including memory inside a computer or other system, or between computers or devices in a system.

The bus forms a communication interface that can communicate with other such devices or any type of device or system to enable multiple distributed devices to intercommunicate or to communicate with a network, for example in a cloud system. Thus, the apparatus can be widely distributed or even ubiquitous, to perform selected local processing regarding usage and environment, for example to enable history tracking, data pre-processing, and sharing to other devices or through the cloud. Usage of optical silicon can enable the apparatus to avoid the bandwidth and bottleneck problems of a system bus.

For example, an optical sensor or silicon-based optical data connection can use silicon photonics and a hybrid silicon laser for communication between integrated circuit chips at distributed locations using plasmons (quanta of plasma oscillation) to communicate over relatively long distances, for example 2-3 inches on a narrow nano-wire coupler. The plasmon is a quasi-particle that results from quantization of plasma oscillations. Data can be received and converted using an optical antenna, a nano-cavity, or a quantum dot. The communication field can travel independently of a wired bus structure.

In some embodiments and/or applications, the apparatus can receive information via the optical link, independently of the system bus connected to a processor, and the apparatus can use the extra-bus information to perform management or housekeeping functions to track applications and/or processes (or, for example, bit correction) via data sent optically to the apparatus. The optical link thus enables low-bandwidth, back-channel communication, enabling formation of a memory that can communicate with large bursts of data for placement with optical accessibility.

The apparatus can use the optical communication interface to substantially increase bandwidth. For example, dynamic random access memory (DRAM) cannot maintain synchrony over a distance of about four inches so that DRAM must be within four inches or less of a communicating processor, resulting in the memory bus becoming a data choke point, which can be relieved by the optical communication interface. Embodiments of the apparatus with an optical interface can use the control logic to perform bus control operations using an optical clock and interferometry using interfering optical beams to accelerate data communication.

In some specific embodiments, the optical silicon interface can be operated by the control logic to increase data communication speed and reliability by constructing signals in the form of a sine-wave in a piece-wise manner, measuring segments above and below a base line and assigning digital values as 0 or 1 depending on wave position. Accordingly, formation of square wave signals is avoided, which attains benefits to heat dissipation, which is proportional to frequency squared.

Instructions can be any suitable type of logic or processor-executable instructions for performing operations and functions in a computer or system that uses the memory. Instructions can specify data handling and memory operations such as handling data in a memory or register (setting a value, moving data, reading and writing data), performing arithmetic and logic operations (add, subtract, multiply, divide, bitwise operations, compare), controlling flow (branch, conditional branch, indirect branch, call), complex instructions (saving to a stack, moving memory blocks, complex arithmetic, floating-point, atomic test and set, combined ALU and operand from memory), and the like.

Figure 9A:
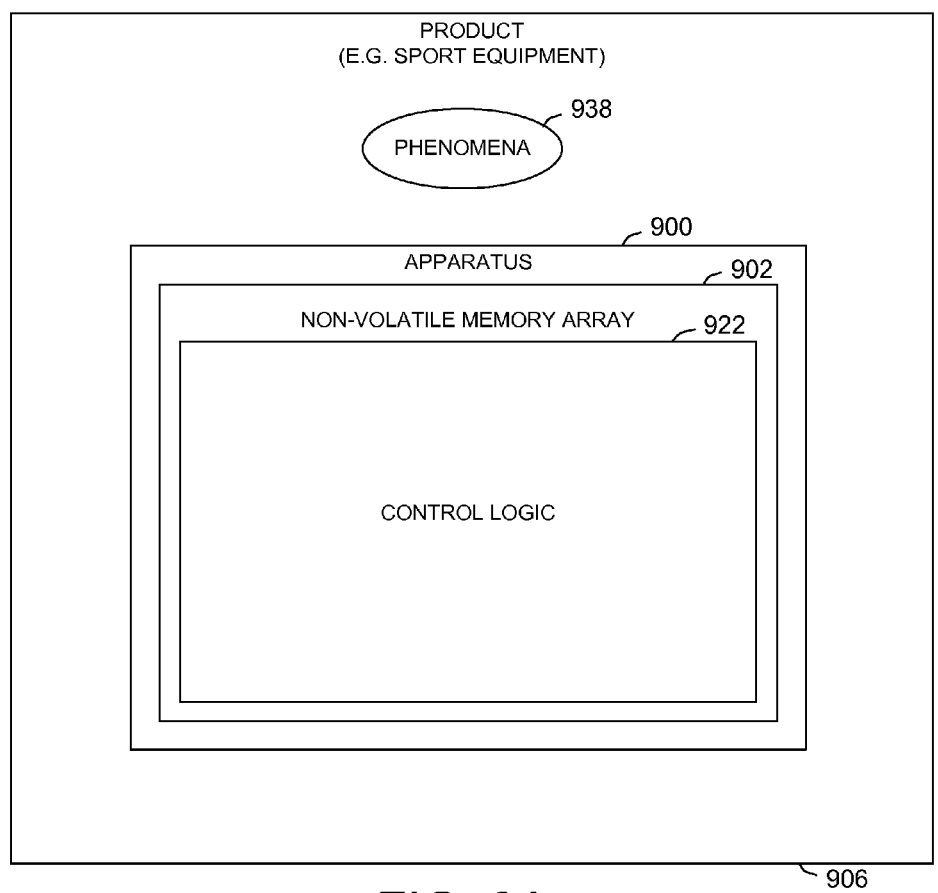
FIGS. 9A and 9B are schematic block diagrams showing respective top and side view of an embodiment of an apparatus including processor and flexible memory that can be integrated universally into a wide variety of products.
Figure 9B:
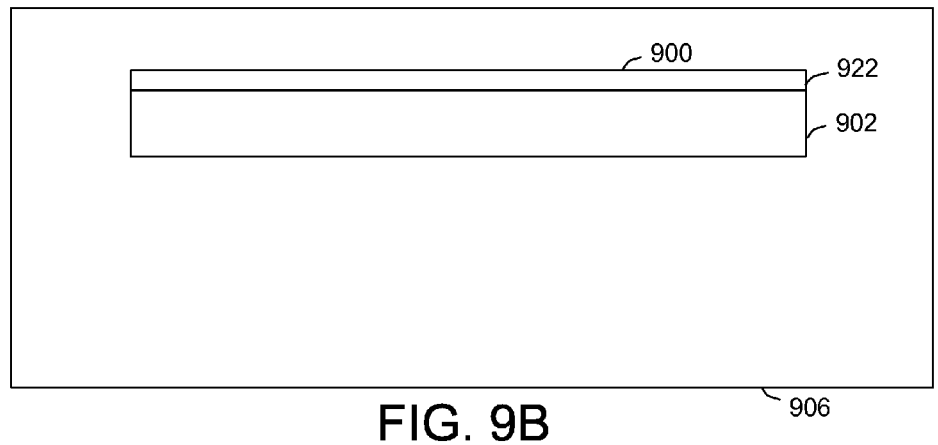

Referring to FIGS. 9A and 9B, schematic block diagrams show respective top and side view of an embodiment of an apparatus including control logic integrated with memory that can be integrated universally into a wide variety of products. Accordingly, the apparatus 900 can include a non-volatile memory array 902 integrated into a product 906 and control logic 922 integrated with and distributed over the non-volatile memory array 902. The control logic 922 can be operable to monitor phenomena 938 detectable at the product 906. For example, the apparatus can be integrated into a product in the form of sporting equipment such as a skateboard, surfboard, snowboard, ski, bicycle, shoes or foot gear, or the like. The control logic and memory can be configured to detect phenomena such as pressure, torsion, temperature, moisture, and the like.

In some embodiments, the apparatus can include some memory that is unacceptable for standard processing but very inexpensive and thus may have some usefulness and cost-effectiveness in some operations. For example, a relatively fast but error-prone memory may be useful for video processing. In various applications, the basis of memory quality may vary, for example, error rate, speed, and the like.

The apparatus can include control logic that facilitates accessing of memory based on a determination of the type of operations being performed. For example, the control logic can detect high traffic in video streaming and modify data handling to shift from 16-bit byte memory accesses to accessing of blocks of data. For cloud computing applications which are limited by bandwidth, the control logic in the locally-controlled apparatus can push all physical parameters off an external processor into the apparatus, avoiding the bandwidth limitation and enabling additional memory-local capability including potentially different error correction algorithms. The apparatus can thus enable a large scale memory with local control, such as a video memory with frame buffers or a dedicated image memory.

In some applications and/or embodiments, the apparatus 900 can be configured such that the control logic 922 operable to monitor phenomena 938 detectable at the product 906 includes control logic 922 operable to accumulate and communicate information about phenomena 938 associated with use of the product 906.

The control store can be configured to enable new operations. For example, the control logic can be configured to facilitate efficient memory accesses. In a particular example, the control logic can support a particular type of special image store which stores information of a particular size and form efficiently in memory, that writes different memory elements concurrently to a value that is suitable according to characteristics of the incoming image data. Special instructions can be used that can efficiently perform transforms on the image data. A memory element can be a memory portion of a predetermined size, a memory portion including a predetermined range of addresses, a memory portion of a predetermined type or technology, a memory portion of a predetermined functionality, a memory portion of a predetermined hierarchical level, a multi-level cell configured to store more than a single bit of information, a single-level cell configured to store a single bit of information, a flip-flop, and the like.

In some embodiments, the apparatus 900 can be formed in which the control logic 922 operable to monitor phenomena 938 detectable at the product 906 includes control logic 922 operable to accumulate and communicate information about phenomena 938 associated with at least one entity in association with the product 906.

In a particular embodiment, the apparatus can include the non-volatile memory array which is inexpensive and can be maintained in close proximity to other types of memory either internal to the apparatus or in a nearby integrated circuit chip. The control logic can be configured to perform bit-error correction by maintaining multiple copies of data in the high capacity enabled by non-volatile memory arrays, rather than the bit-checks of other error correction techniques. The multiple copies of data in the non-volatile memory can be used to occasionally detect errors using the multiple data copies. Accordingly, the apparatus can include a relatively high capacity non-volatile memory array with high capacity and control logic operable to perform error correction. The high capacity in non-volatile memory can be used for error detection and correction in which redundant data is held in the non-volatile memory for error correction in the form of multiple data copies to enable recovery by the receiving memory even when a number of errors up to the capability of the code in use are introduced during transmission or on storage. Errors can be corrected without requesting retransmission by the sender.

In various embodiments, the apparatus 900 can be implemented so that the control logic 922 operable to monitor phenomena 938 detectable at the product 906 includes control logic 922 operable to accumulate and communicate information about phenomena 938 associated with at least one entity in communication with the product 906.

In some embodiments, the apparatus 900 can be arranged in a manner that the control logic 922 operable to monitor phenomena 938 detectable at the product 906 includes control logic 922 operable to accumulate and communicate information about phenomena 938 associated with at least one entity in contact with the product 906.

In some embodiments and/or applications, the apparatus 900 can be composed such that the control logic 922 operable to monitor phenomena 938 detectable at the product 906 includes control logic 922 operable to monitor tactile contact with the product 906.

In particular embodiments, the apparatus 900 can be formed in which the control logic 922 operable to monitor phenomena 938 detectable at the product 906 includes control logic 922 operable to monitor tactile contact with the product 906, determine statistics on type, characteristics, and number of occurrences of tactile contact with the product 906, and store the statistics for access. In particular embodiments, the control logic can perform pattern recognition in an integrated circuit chip and perform analysis in operations that are background to data communication via a bus to a device such as a processor external to the apparatus. Background tasks that are local to the apparatus can include maximum and minimum sorting, medium, and mode computation. Operations perform by the control logic can include statistical measurements, indexing, synchronizing, detection of repetitive tasks, and the like.

In various embodiments and/or applications of the memory device depicted in FIGS. 9A and 9B, the apparatus 900 can be configured such that the control logic 922 operable to monitor phenomena 938 detectable at the product 906 includes control logic 922 operable to monitor conditions of the product 906 independently of commands received from a source external to the product 906. The information or signals received from a device or system external to the apparatus can include commands, executable instructions, codes, a predetermined signal operable as a function for conveying information about the behavior or attributes of a selected phenomenon, or the like. Physical information or signals can be selected from among any quantity exhibiting variation in time, variation in space, an image, or the like that can supply information on the status of a physical system, or convey a message among devices, components, or user. A signal is a physical quantity which varies with time and space and can contain information from source to the destination apparatus. The information or signal is typically transmitted from one or more various locations or sources. In electrical form, the signal can be produced by a transducer that converts the signal from an original form to a waveform expressed as a current, voltage, or electromagnetic waveform, an optical signal, a radio transmission, or the like.

In some embodiments, the apparatus can be configured to respond to time signals. In various embodiments and/or arrangements, the time signal can be selected from among a visible, audible, mechanical, or electronic signal used as a reference to determine time, a clock, a timing pulse, and the like. Workload can refer to impact on the memory device, portions of memory within the memory device, the system containing the memory device, or any predetermined scope relative to the memory device, or the like. Workload can be analyzed and managed according to any selected workload parameters such as memory capacity, memory portion, memory type, memory characteristics, memory operating characteristics, memory availability, processor speed, logic speed, interface or network latency, potential workloads in queue, remaining battery life, energy cost, temperature, location, server type, affinity information, processing time, and the like.

For example, the memory device can include control logic that takes into consideration that, at different times, the loads are expected to be different for management of redundant memory blocks. In a particular instance, the memory device may be used in a data center in which some of the activity is work-related, and other activity is recreational. The control logic can be configured to allocated different types of memory accordingly, for example to handle volumes of streaming video and audio content during non-working hours. In some embodiments, the control logic can manage error detection and/or error correction, for example, to allow more errors without correction for streaming video and audio content.

Figure 10A:
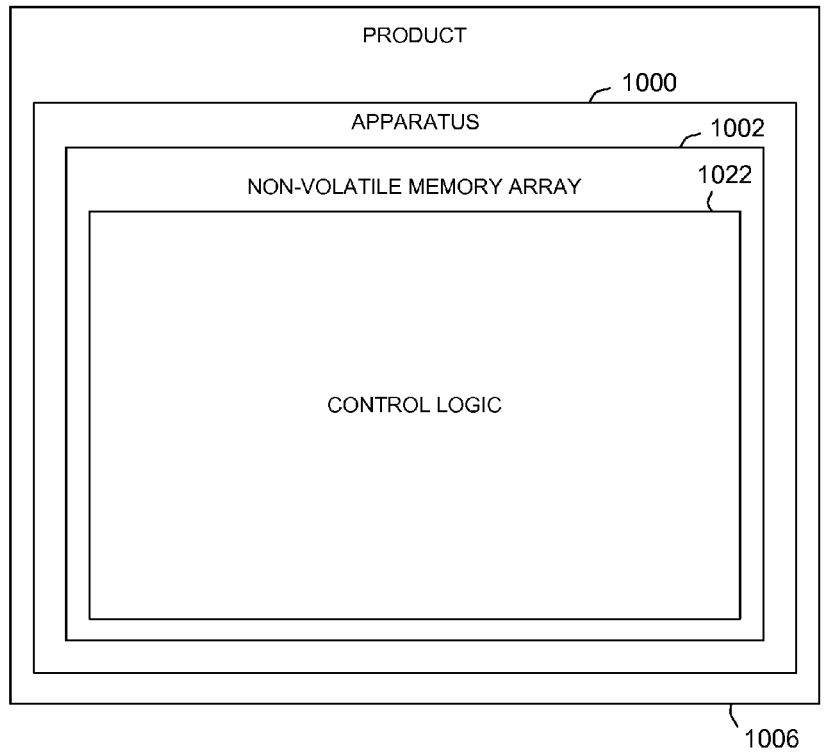
FIGS. 10A and 10B are schematic block diagrams illustrating respective top and side view of an embodiment of an apparatus including processor and flexible memory integrated universally into a product selected from many different products.
Figure 10B:
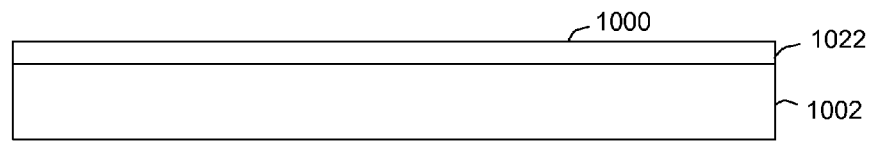

Referring to FIGS. 10A and 10B, schematic block diagrams illustrate respective top and side view of an embodiment of an apparatus including control logic integrated with memory universally into a product selected from many different products. Accordingly, the apparatus 1000 can further include the product 1006 integrated with the non-volatile memory array 1002 and the control logic 1022.

In other example embodiments and/or applications, the control logic can be operable to monitor memory accesses, detect a pattern of instructions and data from the monitored memory accesses, predict expected instructions and data from the detected pattern of instructions and data, and preprocessing the predicted expected instructions. In some applications, the control logic can use the statistics to predict a future sequence of instructions and data. The control logic can detect patterns in which a first sequence of data and/or instructions is commonly followed by a second sequence. Upon detection of such a first sequence, the control logic can apply the second sequence to the memory without actually receiving the second sequence, for example from a processor via the data bus. Thus, the control logic can accelerate data handling and work throughput. The control logic can monitor data and/or instructions and anticipate requests for memory. The control logic can also detect an indexing pattern of instructions and interactions with memory using specialized logic that is integrated into the non-volatile memory area, enabling preprocessing of expected instructions within the memory.

The control logic thus can perform statistical operations that analyze instruction sequences to predict the type of instructions to perform using logic that is distributed within the non-volatile memory arrays of the apparatus.

Figure 11A:
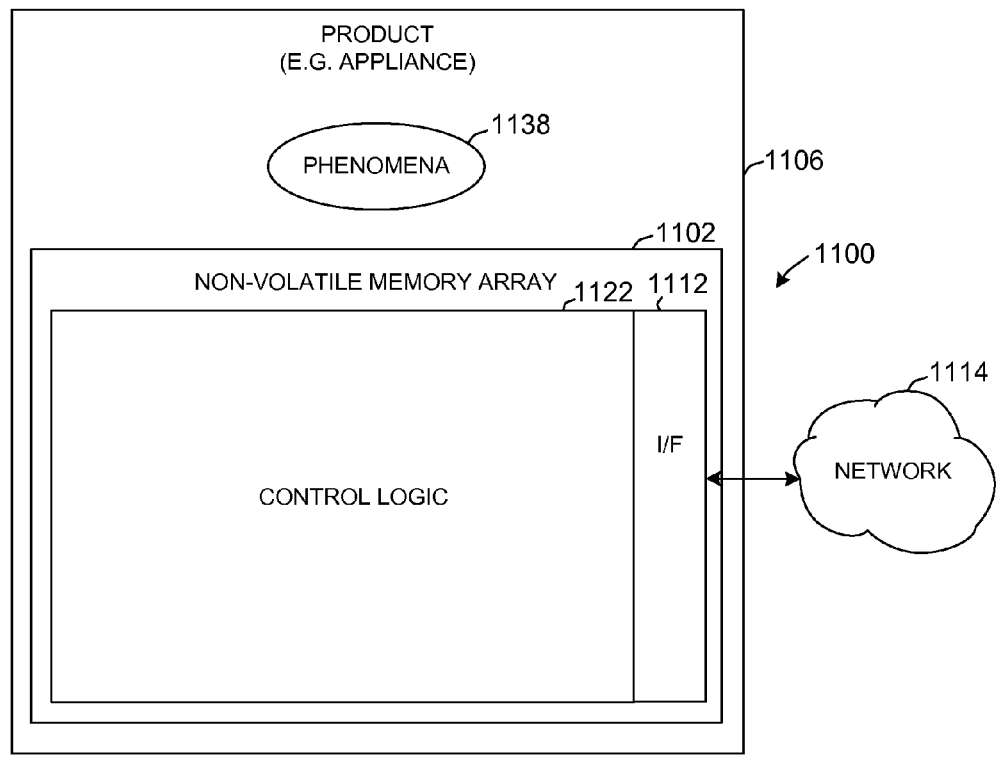
FIGS. 11A and 11B are schematic block diagrams depicting respective top and side view of an embodiment of an apparatus including processor and flexible memory that can be integrated with a communication interface for communication with one or more devices external to the apparatus.
Figure 11B:
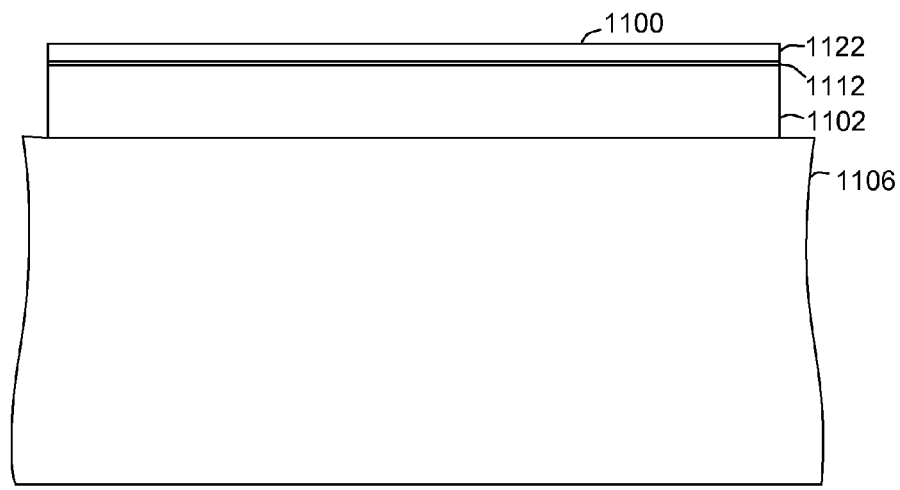

Referring to FIGS. 11A and 11B, schematic block diagrams depict respective top and side view of an embodiment of an apparatus including control logic integrated with memory and a communication interface for communication with one or more devices external to the apparatus. Thus, the apparatus 1100 can further include a communication interface 1112 integrated with the control logic 1122 and the non-volatile memory array 1102, the communication interface 1112 operable for communicating information associated with the phenomena 1138 with a network 1114. For example, the apparatus can be integrated into a product in the form of an appliance such as a refrigerator, freezer, oven, washer, dryer, or the like. The control logic integrated with the memory can be configured to monitor phenomena such as refrigerator or freezer supplied power, temperature in one or more compartments, and the like. The information relating to the phenomena can be communicated via a network to assist in determination of operating conditions, power or resource conservation, spoilage, and the like.

Figure 12A:
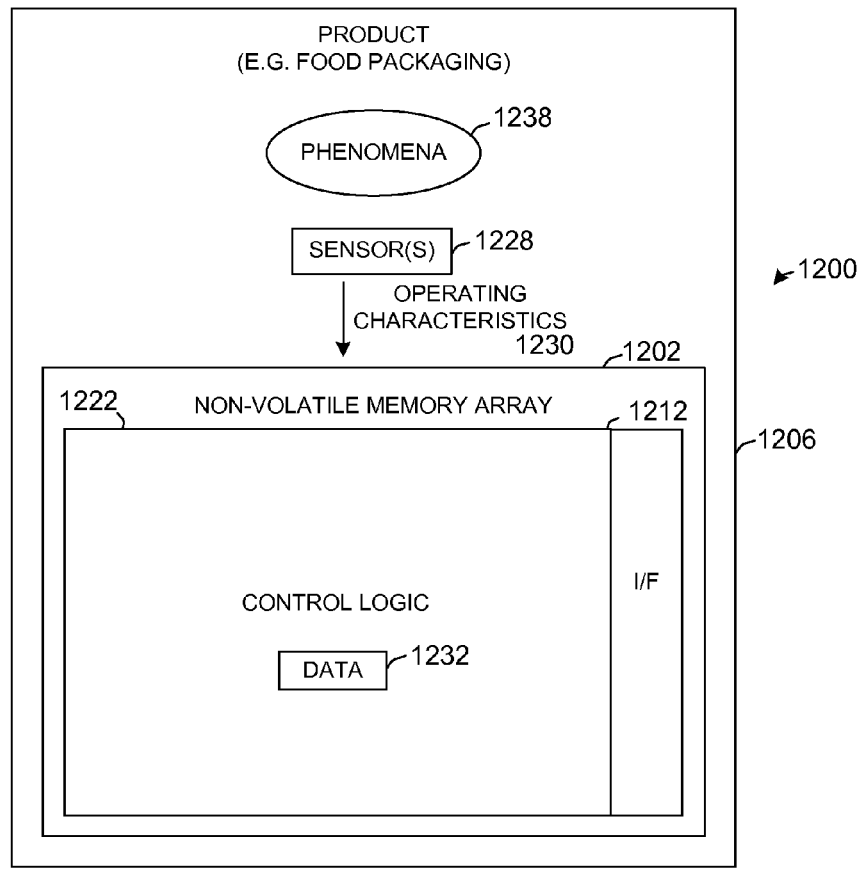
FIGS. 12A and 12B are respective top and side views of schematic block diagrams illustrating embodiments of an apparatus including control logic integrated with memory that is capable of operating in combination with one or more sensors integrated with the apparatus to detect and react to operating conditions.
Figure 12B:

Referring to FIGS. 12A and 12B, respective top and side views of schematic block diagrams illustrate embodiments of an apparatus including control logic integrated with memory that is capable of operating in combination with one or more sensors integrated with the apparatus to detect and react to operating conditions. For example, the apparatus can be integrated into a product in the form of food packaging. The apparatus can include any suitable type of sensor for determining chemical content, moisture, temperature, and the like. The control logic and memory can be configured to facilitate monitoring of food composition, quality, or freshness.

Figure 13A:
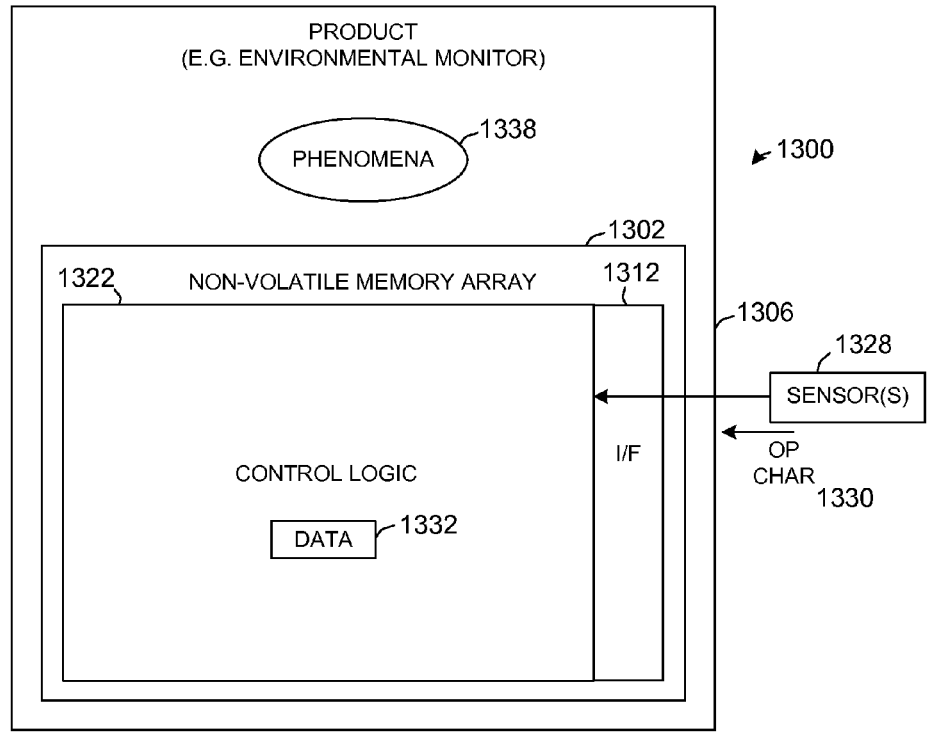
FIGS. 13A and 13B are respective top and side views of schematic block diagrams showing embodiments of an apparatus including control logic integrated with memory that is capable of operating in combination with one or more sensors external to the apparatus to detect and react to operating conditions.
Figure 13B:
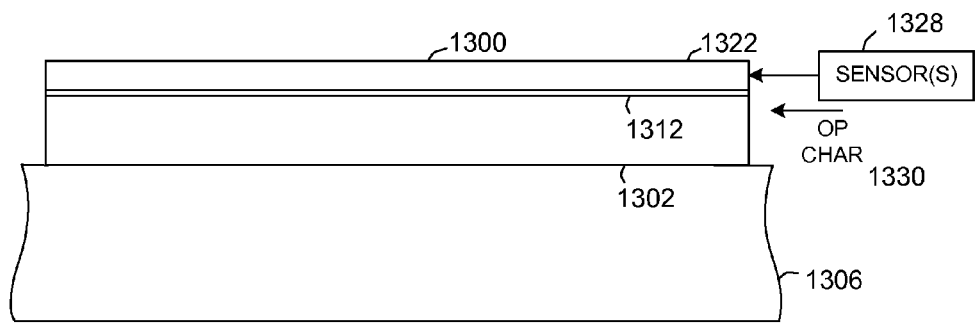

Referring to FIGS. 13A and 13B, respective top and side views of schematic block diagrams show embodiments of an apparatus including control logic integrated with memory that is capable of operating in combination with one or more sensors external to the apparatus to detect and react to operating conditions. For example, the apparatus can be integrated with a product in the form of a currency counter, money drawer, or the like. The apparatus can include any suitable type of sensor such as light or color detecting sensor, optical pattern sensor, or the like. The control logic and memory can be configured to detect currency denomination and validity (whether counterfeit).

Accordingly, the apparatus 1200, 1300 can further include at least one sensor 1228, 1328 operable to detect an operating condition 1230, 1330 of the product 1206, 1306. The control logic 1222, 1322 operable to monitor phenomena 1238, 1338 detectable at the product 1206, 1306 can include control logic 1222, 1322 operable to monitor the operating condition 1230, 1330.

In some embodiments and/or applications, the apparatus 1200, 1300 can further include at least one sensor 1228, 1328 operable to detect an operating condition 1230, 1330 of the product 1206, 1306. The control logic 1222, 1322 operable to monitor phenomena 1238, 1338 detectable at the product 1206, 1306 can include control logic 1222, 1322 operable to monitor the operating condition 1230, 1330, derive data 1232, 1332 from the operating condition 1230, 1330, process data 1232, 1332 derived from the operating condition 1230, 1330, and store the processed data 1232, 1332.

In various embodiments, the apparatus 1200, 1300 can further include a communication interface 1212, 1312 integrated with the control logic 1222, 1322 and the non-volatile memory array 1202, 1302 and at least one sensor 1228, 1328 operable to detect an operating condition 1230, 1330 of the product 1206, 1306. The control logic 1222, 1322 operable to monitor phenomena 1238, 1338 detectable at the product 1206, 1306 can include control logic 1222, 1322 operable to monitor the operating condition 1230, 1330, derive data 1232, 1332 from the operating condition 1230, 1330, process data 1232, 1332 derived from the operating condition 1230, 1330, and communicate the processed data 1232, 1332 via the communication interface 1212, 1312.

Figure 14:
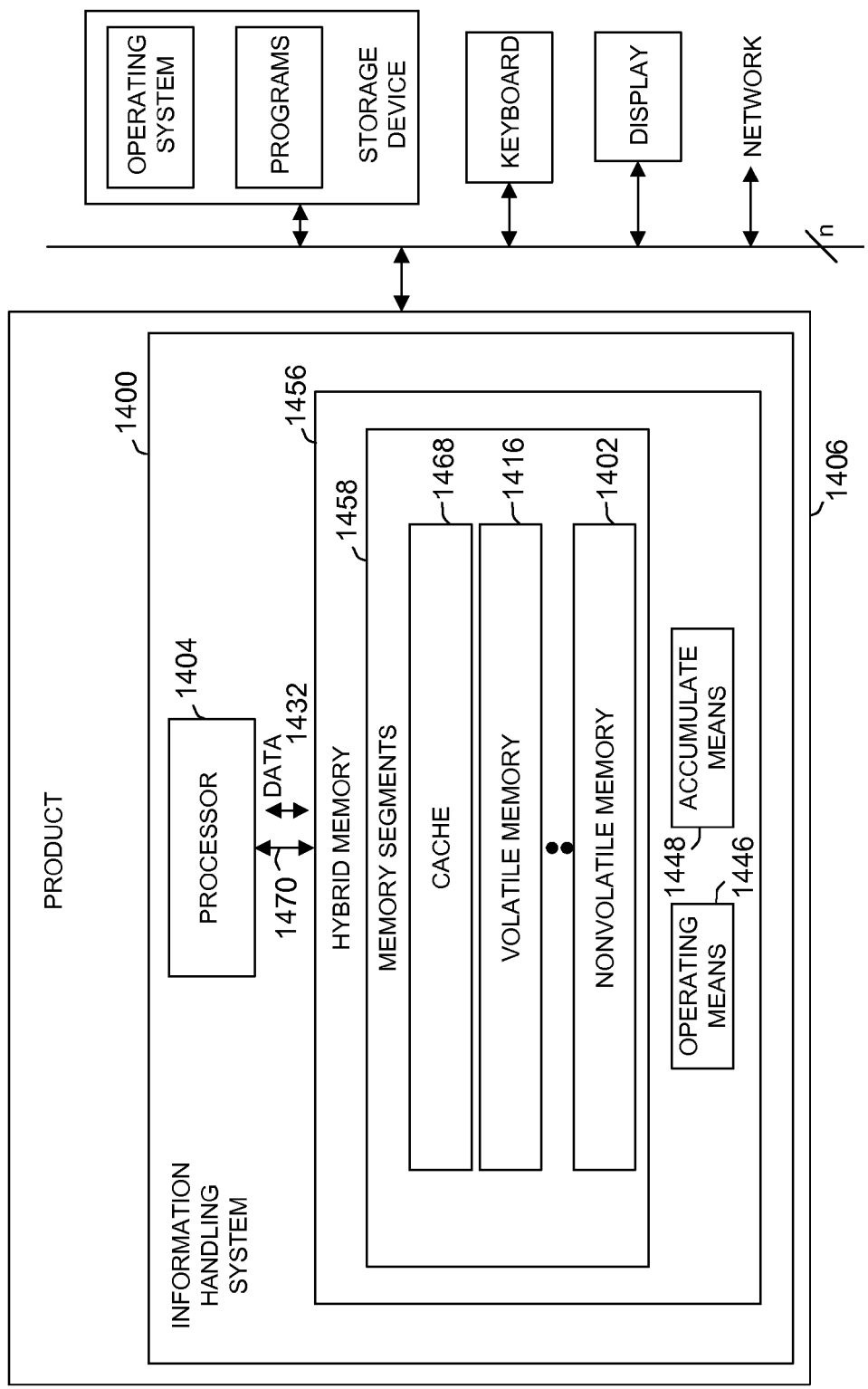
FIG. 14 is a schematic block diagram showing an embodiment of an information handling system including a processor integrated with memory configured for integration with a product.

Referring to FIG. 14, a schematic block diagram shows an embodiment of an information handling system including a processor integrated with memory configured for integration with a product. Accordingly, in further embodiments, as depicted in FIG. 14, an information handling system 1400 can include means 1446 for operating a processor 1404 integrated with a non-volatile memory array 1402, and means 1448 for accumulating information associated with a product 1406.

In an example embodiment, the information handling system 1400 can include a hybrid memory 1456 that includes multiple memory segments 1458 characterized by a multiple different operating characteristics. The hybrid memory 1456 can store data 1432 communicated from a processor 1404. The information handling system 1400 can further include logic for performing encryption operations on the data 1432 during transfers between the memory segments 1458.

In some embodiments, the information handling system 1400 can be constituted wherein the logic operable to perform encryption operations is operable to perform encryption operations on the data 1432 during transfers between the processor 1404 and the multiple memory segments 1458.

The multiple memory segments 1458 can be arranged to include various types of memory with different characteristics and speeds, for example the multiple memory segments 1458 can comprise volatile main memory 1416, non-volatile main memory 1402, or a combination of memory types.

In various embodiments, the information handling system can include multiple types of memory technology, for example including charge memory or resistive memory. An information handling system can include sections of charge memory and resistive memory and the control logic can assign applications to exploit the advantages and diminish the consequences of disadvantages of either type of memory. Charge memories induce a voltage which is detected during read operations in response to require amounts of charge. In nonvolatile storage, flash memories precisely control the discrete charge placed on a floating gate. In volatile storage, DRAM not only places charge in a storage capacitor but also mitigate subthreshold charge leakage through the access device using capacitors that are sufficiently large to store charge for reliable sensing and using transistors that are sufficiently large to exert effective control over the channel. Resistive memories use electrical current to induce a change in atomic structure, changing the resistance detected during reads. Resistive memories are more suitable for scaling than charge memories by avoiding precise charge placement and control. Programming via techniques such as current injection scale with cell size. Phase-change memory (PCM), spin-torque transfer (STT) magneto-resistive RAM (M-RAM), and ferroelectric RAM (FRAM) are examples of resistive memories.

The non-volatile memory array can include memory portions formed of memory technologies characterized by high performance under particular operating conditions. Phase change RAM (PCRAM) is a memory technology with highly favorable small cell size and thus density. The information handling system which includes at least a portion of PCRAM can further include control logic that monitors and determines operating conditions and can assign memory accesses to PCRAM in low power high performance conditions.

Other examples of non-volatile memory technologies with various QoS ratings can include resistive RAM (R-RAM) and spin-transfer torque RAM (STT-RAM). R-RAM can be any memory technology that relies of resistance change to store information, for example including space-charge-limited-current (SCLC), filament, programmable-metallization-cell (PMC), Schottkey contact and traps (SCT). R-RAM can be characterized by non-volatility, high-speed, high-performance, zero standby power, and, in some arrangements, high density. For an information handling system that includes at least a portion of the memory in the form of R-RAM, the control logic can monitor memory accesses and determine whether a particular application is characterized by high-speed and high-performance, and assign the R-RAM memory portion for the application.

In another example application, an information handling system can include a non-volatile memory array and includes at least a portion of the memory in the form of STT-RAM. STT-RAM can be characterized by improved performance via overdriving. Overdriving the gate voltage of an NMOS transistor in the STT-RAM can increase $V_{GS}$ and thus enhance the driving strength of the NMOS transistor. The control logic can be configured to manage overdriving, for example, by monitoring memory access operations such as reading, writing, erasing, driving write-line voltage, and the like, and control overdriving according to the particular application.

In particular embodiments, the multiple memory segments 1458 can constitute a volatile main memory 1416 and a non-volatile main memory 1402 wherein the volatile main memory 1416 has faster operating characteristics than the non-volatile main memory 1402. For example, the multiple memory segments 1458 can be formed in memory subsystem combining DRAM and a large amount of nonvolatile memory such as flash or phase change memory (PCM).

In some information handling system 1400 embodiments, the multiple memory segments 1458 can include a cache 1468. In an example embodiment, DRAM can operate as a cache 1468 for the PCM or nonvolatile memory, facilitating channel encryption between the processor 1404 and the information handling system 1400. The logic operable to perform encryption operations can decrypt the information encrypted by the processor 1404 and sent over the channel and store the decrypted information in the DRAM, then can use storage encryption when passing the information from the DRAM to the PCM or nonvolatile memory 1402.

Various embodiments of the information handling system 1400 can be configured for channel encryption. For instance, the logic operable to perform encryption operations can function to encrypt data 1432 on a communication channel 1470 that communicates information between the processor 1404 and the hybrid memory 1456.

The information handling system 1400 can be configured to perform one or more of several channel encryption operations in cooperation with a processor 1404. For instance, the logic operable to perform encryption operations can operable to decrypt information encrypted by the processor 1404. In some embodiments and/or conditions, the logic operable to perform encryption operations is operable to decrypt address and data information encrypted by the processor 1404 and store data at the address in the hybrid memory 1456. Similarly, the information handling system 1400 can be configured wherein the logic operable to perform encryption operations is operable to partially decrypt information encrypted by the processor 1404.

Some embodiments of the information handling system 1400 can include a random number generator, for example which can be closely associated to and integrated onto the information handling system 1400 chip. Accordingly, the processor 1404 can implement a pseudo-random number generator coupled to the hybrid memory 1456 and coupled to the logic operable to perform encryption operations. The pseudo-random number generator can be operable to generate numbers for usage in encrypting information.

The information handling system 1400 can be configured to implement one or more of a variety of security schemes including channel encryption, storage encryption, RSA (Rivest, Shamir, Adleman) cryptography and key distribution, Public Key Infrastructure (PKI). Accordingly, the logic operable to perform encryption operations can be operable to perform stream encryption of communicated information wherein processor and memory sides are assigned a key. In another example functionality, the logic operable to perform encryption operations can be operable to encrypt information that is storage encrypted wherein the storage-encrypted information is encrypted by the processor 1404, stored in the hybrid memory 1456, accessed from the hybrid memory 1456, and decrypted by the processor 1404.

In some embodiments and/or applications, the information handling system 1400 can be configured to use of cryptographic processing to facilitate information handling. For example, data can be copied for redundant storage and the redundant copy can be secured by encryption and stored in the non-volatile memory in encrypted form. The encrypted redundant copy of the data can be used for restoration in the event of a detected error. In another example, A cryptographic hash function generates information indicative of data integrity, whether changes in data are accidental or maliciously and intentional. Modification to the data can be detected through a mismatching hash value. For a particular hash value, finding of input data that yields the same hash value is not easily possible, if an attacker can change not only the message but also the hash value, then a keyed hash or message authentication code (MAC) can supply additional security. Without knowing the key, for the attacker to calculate the correct keyed hash value for a modified message is not feasible.

In a particular applications and/or arrangements, the security perimeter can be formed within the information handling system 1400 and, for example, enclose the entire information handling system 1400, between dynamic random access memory (DRAM) and the information handling system 1400, between non-volatile random access memory (RAM) and the information handling system 1400, or any other suitable position. The cryptographic and/or tamper-handling perimeter can further be generalized for positioning between a smaller amount of memory and a larger amount of memory in the information handling system 1400. Some embodiments can include a cryptographic perimeter in the absence of a tamper-handling perimeter.

In some embodiments, the logic operable to perform encryption operations can be operable to perform time-varying encryption. For example, channel encryption assisted by the information handling system 1400 can enable randomization of encrypted information wherein encrypted data is read back and encryption can be stripped off by the receiving processor 1404. The information handling system 1400 with logic or other smart component can enable time-varying encryption. Data can be written to an address which, when read back, is different, but no information is lost since the reading processor 1404 or other reading device at the opposite side of the channel from the smart memory has sufficient intelligence capability to strip off the encryption.

In an example embodiment, the information handling system can include control logic can allocate writes according to memory type. For example, the information handling system can include a section of PCRAM. Writes can result in substantial wear in PCRAM. When current is injected into a volume of phase-change material, thermal expansion and contraction degrade the electrode storage contact, resulting in programming currents injected into the memory cell that are insufficiently reliable. PCRAM material resistivity is highly dependent on current injection so that current variability leads to resistance variability, degrading the read window of suitable programmed minimum and maximum resistances. Accordingly, the control logic and monitor and determine applications characterized by repeated and enduring writes, and allocate such applications to memory segments other than PCRAM segments.

A information handling system can be configured with control logic that is operable to mitigate wear and energy. For example, PCRAM, which is susceptible to wear and failure for high levels of writing to a PCRAM cell over a memory lifetime, can be managed using mitigation techniques of write reduction and leveling to improve PCRAM endurance. In a particular operation, the control logic can allocate some memory to function as a cache and track written cache lines and written cache words to implement partial writes and reduce wear. In another technique, the control logic can monitor writes to eliminate redundant bit writes. In a typical memory access, a write updates an entire row of memory cells, many of which are redundant. The control logic can remove the redundant bit writes and thereby substantially increase memory lifetimes, for example by preceding a write with a read and compare. Following the read, an XNOR gate can be used to filter redundant bit-writes. A PCRAM read is sufficiently faster than a PCM write and writes are less latency critical, so the performance reduction from reading before a write is inconsequential.

In some embodiments and/or applications, the control logic can allocate instruction cache and data cache depending on the application and environment. In further arrangements, the control logic can also select physical locations of memory depending on application and operating environment.

In addition to eliminating redundant writes, the control logic can also improve write wear performance by row shifting. After removing redundant bit writes, bits most written in a row tend to be localized so that the control logic can perform simple shifting to more evenly distribute writes within a row.

The control logic can attain additional wear improvement by segment swapping in which memory segments of high and low write accesses are periodically swapped. The control logic can track write counts and manage a mapping table between segments.

In another example embodiment, the information handling system can include control logic operable to allocate memory according to wear such as by limiting the frequency of allocation for a particular memory block and by maintaining frequently changing metadata in DRAM that is separate from managed blocks of non-volatile memory.

Embodiments of the information handling system can perform wear-leveling via managed allocation. For example, the control logic can avoid allocation of a newly released memory block but rather time-stamp the block and add the block to a first-in-first-out queue. On subsequent allocations or releases, the control logic can examine the block at the head of the queue and, if resident on the queue for a sufficient time, can remove the block from the queue and mark eligible for re-allocation. The control logic can maintain list pointers in headers and footers of freed blocks and update the list pointers when adjacent free blocks are merged into a larger free region. In another technique, the control logic can track the allocated or free state of memory blocks using a DRAM bitmap and manage the bitmap dynamically during operations.

Figure 15A:
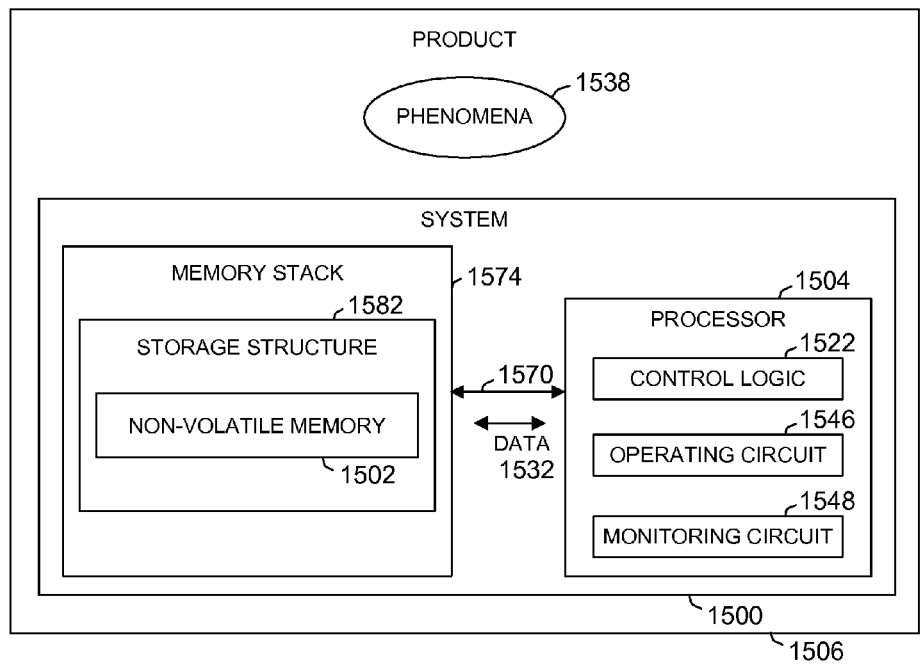
FIGS. 15A and 15B are a schematic block diagram and a side pictorial view illustrating an embodiment of a system formed of circuitry that includes control logic integrated with memory into a product selected from a wide variety of products.
Figure 15B:
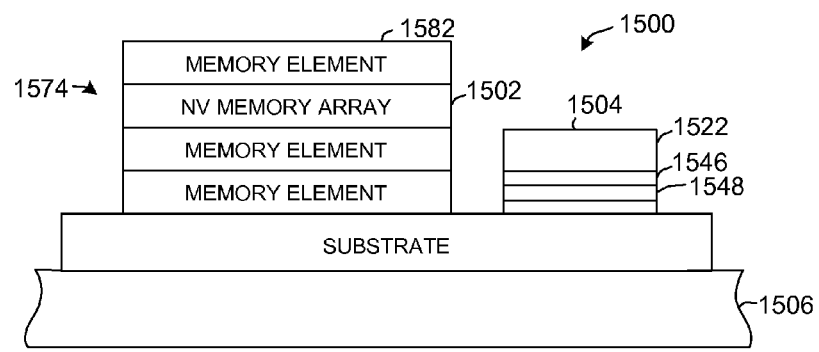

Referring to FIGS. 15A and 15B, a schematic block diagram and a side pictorial view illustrate an embodiment of a system formed of circuitry that includes control logic integrated with memory into a product selected from a wide variety of products. An embodiment of a system 1500 can include circuitry 1546 for operating a control logic 1522 integrated with and distributed over a non-volatile memory array 1502 and integrated into a product 1506, and circuitry 1548 for monitoring phenomena 1538 detectable at the product 1506.

Embodiments of a system 1500 can make use of a memory stack 1574 to facilitate intelligent memory computation. In a particular example embodiment, intelligent memory computation can include security capabilities, including cryptographic security. The system 1500 can be constituted to facilitate channel encryption through operation of the logic operable to perform encryption operations. Accordingly, the logic operable to perform encryption operations can be operable to perform channel encryption operations on a communication channel 1570 that communicates information between the processor 1504 and the memory stack 1574. Channel encryption can improve performance and economy in various applications and conditions in comparison to expensive storage encryption. The logic operable to perform encryption operations can facilitate good memory encryption, for example between the processor 1504 and the memory stack 1574. An illustrative configuration can include a CPU that interacts with the memory stack 1574 comprising multiple DRAM chips and the logic operable to perform encryption operations integrated into a logic chip operable to perform strong channel encryption between the CPU and the memory stack 1574.

In various embodiments, the system 1500, the memory stack 1574, and the logic operable to perform encryption operations can be constituted to perform one or more of several security operations. For example, the logic operable to perform encryption operations is operable to decrypt information encrypted by the processor 1504. Similarly, the logic operable to perform encryption operations is operable to partially decrypt information encrypted by the processor 1504. The logic can also be operable to perform encryption operations is operable to perform stream encryption of information communicated on a communication channel 1570 wherein processor and memory sides of the communication channel 1570 are assigned a key. In an embodiment or circumstances where security can be best attained by using a combination of storage encryption and channel encryption, the logic operable to perform encryption operations is operable to perform channel encryption operations on a communication channel 1570 for information that is storage encrypted wherein the storage-encrypted information is encrypted by the processor 1504, stored in the memory stack 1574, accessed from the memory stack 1574, and decrypted by the processor 1504. The logic operable to perform encryption operations can also be operable to perform time-varying encryption.

Information can be stored in the memory stack 1574 unencrypted or the logic can encrypt the data for storage. Thus, channel encryption can be performed between the CPU and a logic chip, enabling cryptographic security without requiring storage encryption of data stored in the logic chip.

Various techniques may be used for forming an integrated circuit with a combination of the non-volatile memory array and the control logic. In one example technique, an integrated circuit for a non-volatile memory cell transistor can be formed by constructing a layer of discrete storage cells over a substrate in two substrate regions, applying a dielectric layer over the layer of discrete storage cells in the two substrate regions, and building a barrier layer over the dielectric layer in the two regions. The barrier layer, dielectric layer, and the layer of discrete storage cells are then removed in one of the two substrate regions, leaving the layers intact in the other of the two substrate regions. An additional barrier layer is then formed over the substrate in the two substrate regions, then removed from the substrate region from which the barrier layer, dielectric layer, and the layer of discrete storage cells were previously removed. Two gates of a memory element are then formed respectively in the two substrate regions with one gate including a portion of the first barrier layer and another gate including a portion of the additional barrier layer. One aspect of fabricating a circuit that integrates the non-volatile memory array and the control logic on the system is selection of a suitable annealing process. For example, the illustrative integrated circuit can include a charge storage layer and a barrier layer formed over both a non-volatile memory region and a logic region. The charge storage layer can be formed of one or more layers and can include multiple discrete storage cells for storing charge which are isolated by a dielectric layer of insulating material with a suitably high dielectric constant. The charge storage layer can be constructed by depositing and annealing the discrete storage cells (for example, one or more of a silicon material such as polysilicon, silicon carbide, or the like, or a suitable metal such as germanium) on a dielectric area. The thermal annealing action can be performed by rapid thermal annealing (RTA) or a slower annealing process such as laser spike annealing (LSA). Memory properties can be selected and controlled by optimizing the annealing condition, thereby resulting in an improved reliability, write durability, and failure resistance.

In another example technique for forming an integrated circuit with a combination of the non-volatile memory array and the control logic, a non-volatile memory cell with improved charge retention on a substrate common with logic devices using a single-gate logic process in which a silicide-blocking dielectric barrier is formed over a floating gate of a non-volatile memory cell so that silicide cannot be formed over the floating gate but is formed over logic devices, thereby preventing bridging and silicide spiking in the non-volatile memory cell. The silicide-blocking dielectric barrier prevents silicide metal from contacting the floating gate or sidewall spacers while allowing the silicide metal in parts of active regions of the non-volatile memory cell at locations removed from the floating gate and spacers. The silicide regions can be constructed by initially depositing a refractory metal layer over the surface of the non-volatile memory cell, followed by a reactive anneal which causes the metal layer to react with the underlying contacted silicon regions to form silicide regions. A metal strip removed unreacted portions of the metal layer but leaves the silicide regions which are formed by a logic process using metals such as titanium, cobalt, nickel, or the like. A relatively slow annealing process can be used to produce suitable memory performance.

In a further example technique for forming an integrated circuit with a combination of the non-volatile memory array and the control logic, a scalable, logic transistor can be constructed with drain and source formed as a pair of doped regions and a gate insulator layer formed over the substrate and between the drain and source. A gate stack can include a gate layer (polysilicon or metal) between two metal nitride layers. A non-volatile memory transistor that is compatible with the logic transistor can be added via a high-K dielectric constant film with an embedded metal nano-dot layer between a tunnel insulator and the gate stack. The drain and source doped regions can be n+ regions doped into a p-type substrate to form an n-channel Field Effect Transistor (FET) device. The diffusion regions can be formed using n+ doped amorphous silicon, followed by an anneal such as a rapid thermal anneal (RTA) to reduce thermal budget and silicidation. A p-channel FET can similarly be formed via p+ diffusion source/drain regions applied over an n-well region. In other embodiments, annealing can be performed using a slow annealing process to improve memory performance and write durability while reducing stress and defects.

In an additional example technique for forming an integrated circuit with a combination of the non-volatile memory array and the control logic, non-volatile memory process steps can be added to a processor for forming high-voltage complementary metal-oxide semiconductor (CMOS) devices. The fabrication technique can include formation of isolation areas for the non-volatile memory and the high-voltage CMOS elements, forming high thermal drive process elements of both the memory and CMOS cells, forming mid thermal drive process elements of the logic CMOS cells, and forming low thermal process elements for logic CMOS, non-volatile memory, and high-voltage CMOS cells. Dopants for forming the devices can include masked implantation of boron, phosphorus and other species and subsequent annealing of the dopings, for example, using a slow annealing process to enhance charge retention in the system.

The non-volatile memory can be formed of one or more of any non-volatile memory type or technology including read-only memory, flash memory, ferroelectric random access memory (F-RAM), magneto-resistive RAM (M-RAM) or the like.

Referring to FIGS. 16A through 16V and FIGS. 17A through 17B, multiple schematic flow charts show several embodiments and/or aspects of a method of operating an apparatus including memory and a processor integrated into a product. The illustrative method 1600, depicted in FIG. 16A, of operating an apparatus can include providing 1601 a processor integrated with a non-volatile memory array and the apparatus, operating 1602 the processor in combination with the non-volatile memory array, and accumulating 1603 information associated with a product.

Referring to FIG. 16B, in some embodiments, a method 1604 of operating the apparatus can further include providing 1605 the product integrated with the non-volatile memory array and the processor.

In further embodiments and/or applications, as shown in FIG. 16C, the method 1606 of operating the apparatus can further include accumulating 1607 information about use of the product, and communicating 1608 the information about the use of the product.

Figures 16D, 16E, 16F:
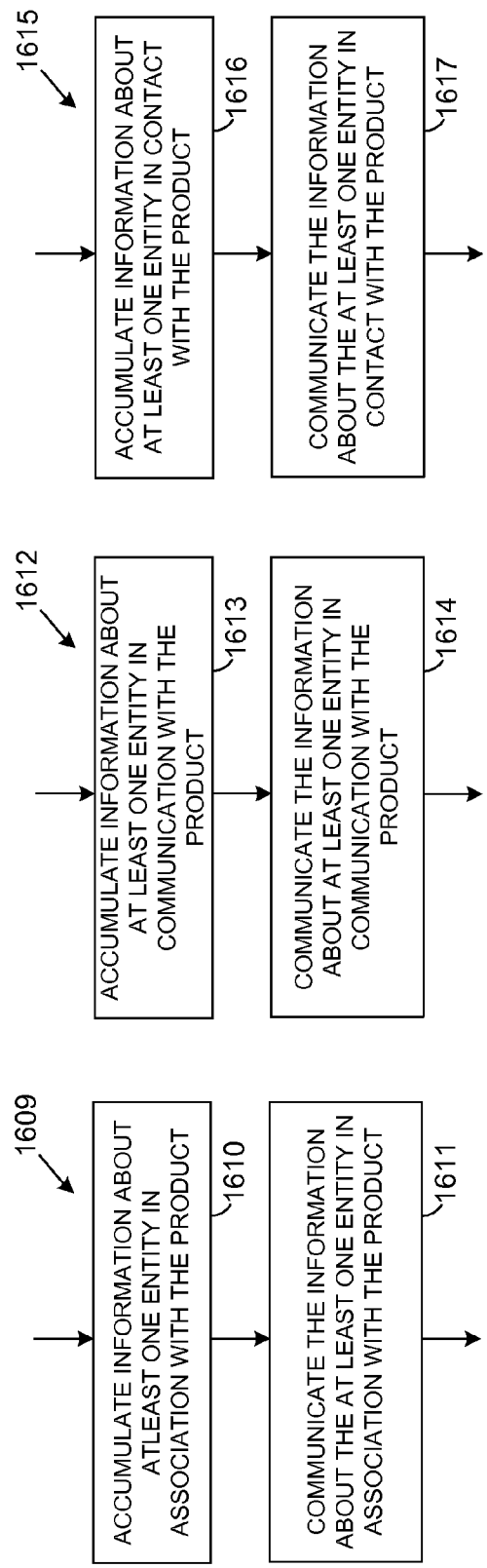
FIGS. 16A through 16V and FIGS. 17A through 17B are multiple schematic flow charts depicting several embodiments and/or aspects of a method of operating an apparatus including memory and a processor integrated into a product.

In various embodiments, as depicted in FIG. 16D, the method 1609 of operating the apparatus can further include accumulating 1610 information about at least one entity in association with the product, and communicating 1611 the information about the about the at least one entity in association with the product.

Referring to FIG. 16E, in some embodiments, the method 1612 of operating the apparatus can further include accumulating 1613 information about at least one entity in communication with the product, and communicating 1614 the information about the about the at least one entity in communication with the product.

As shown in FIG. 16F, in various embodiments and/or applications, the method 1615 of operating the apparatus can further include accumulating 1616 information about at least one entity in contact with the product, and communicating 1617 the information about the about the at least one entity in contact with the product.

In some embodiments, illustrated in FIG. 16G, the method 1618 of operating the apparatus can further include providing 1619 the processor integrated with the non-volatile memory array onto a printed polymer and the product.

In various embodiments and/or applications, as shown in FIG. 16H, the method 1620 of operating the apparatus can further include providing 1621 the processor integrated with the non-volatile memory array onto a printed flexible polymer and the product.

Referring to FIG. 16I, selected embodiments of the method 1622 of operating the apparatus can further include providing 1623 a communication interface integrated with the processor and the non-volatile memory array, and communicating 1624 with a network using the communication interface.

As illustrated in FIG. 16J, some embodiments of the method 1625 of operating the apparatus can further include providing 1626 a communication interface integrated with the processor and the non-volatile memory array, communicating 1627 with a network using the communication interface, and operating 1628 the processor. Operating 1628 the processor can include performing 1629 data preprocessing, performing 1630 history tracking, and managing 1631 data and history communication.

As shown in FIG. 16K, an embodiment of the method 1632 of operating the apparatus can further include providing 1633 a volatile memory integrated with the non-volatile memory array and the processor.

Referring to FIG. 16L, in some embodiments, the method 1634 of operating the apparatus can further include operating 1635 the processor including monitoring 1636 tactile contact with the product.

In further embodiments and/or applications, as shown in FIG. 16M, the method 1637 of operating the apparatus can further include operating 1638 the processor including monitoring 1639 tactile contact with the product, determining 1640 statistics on type, characteristics, and number of occurrences of tactile contact with the product, and storing 1641 the statistics for access.

In various embodiments, as depicted in FIG. 16N, the method 1642 of operating the apparatus can further include operating 1643 the processor including monitoring 1644 conditions of the product independently of commands received from a source external to the product.

Referring to FIG. 16O, in some embodiments, the method 1645 of operating the apparatus can further include providing 1646 the non-volatile memory array partitioned into a plurality of memory blocks, providing 1647 the processor partitioned into control logic arranged into a plurality of command logic blocks spatially distributed over the non-volatile memory array, and associating 1648 ones of the plurality of command logic blocks with ones of the plurality of memory blocks.

As shown in FIG. 16P, in various embodiments and/or applications, the method 1649 of operating the apparatus can further include providing 1650 the processor including control logic, providing 1651 the control logic integrated with the non-volatile memory array, providing 1652 the control logic distributed over the non-volatile memory array, and operating 1653 the control logic. Operating 1653 the processor can include selectively distributing 1654 functionality across the non-volatile memory array.

In some embodiments, illustrated in FIG. 16Q, the method 1655 of operating the apparatus can further include providing 1656 the processor including control logic, providing 1657 the non-volatile memory array arranged in a plurality of memory blocks characterized by a plurality of different operating characteristics, and operating 1658 the control logic. Operating 1658 the processor can include selectively distributing 1659 functionality over the plurality of memory blocks.

In various embodiments and/or applications, as shown in FIG. 16R, the method 1660 of operating the apparatus can further include providing 1661 the processor including control logic, providing 1662 the non-volatile memory array arranged in a plurality of memory blocks characterized by a plurality of different operating characteristics, and operating 1663 the control logic. Operating 1663 the processor can include analyzing 1664 conditions of the product, and selectively distributing 1665 functionality over the plurality of memory blocks based on the analysis.

Referring to FIG. 16S, selected embodiments of the method 1666 of operating the apparatus can be further arranged to include providing 1667 the processor including control logic, providing 1668 at least one sensor integrated into the apparatus, detecting 1669 an operating condition of the product based on signals received from the at least one sensor, and operating 1670 the control logic. Operating the processor 1670 can include monitoring 1671 the operating condition.

Referring to FIG. 16T, in some embodiments, the method 1672 of operating the apparatus can be carried out to further include providing 1673 the processor including control logic, detecting 1674 an operating condition of the product based on signals received from at least one sensor, and operating 1675 the control logic. Operating 1675 the processor can include monitoring 1675 the operating condition.

Figures 16U, 16V:
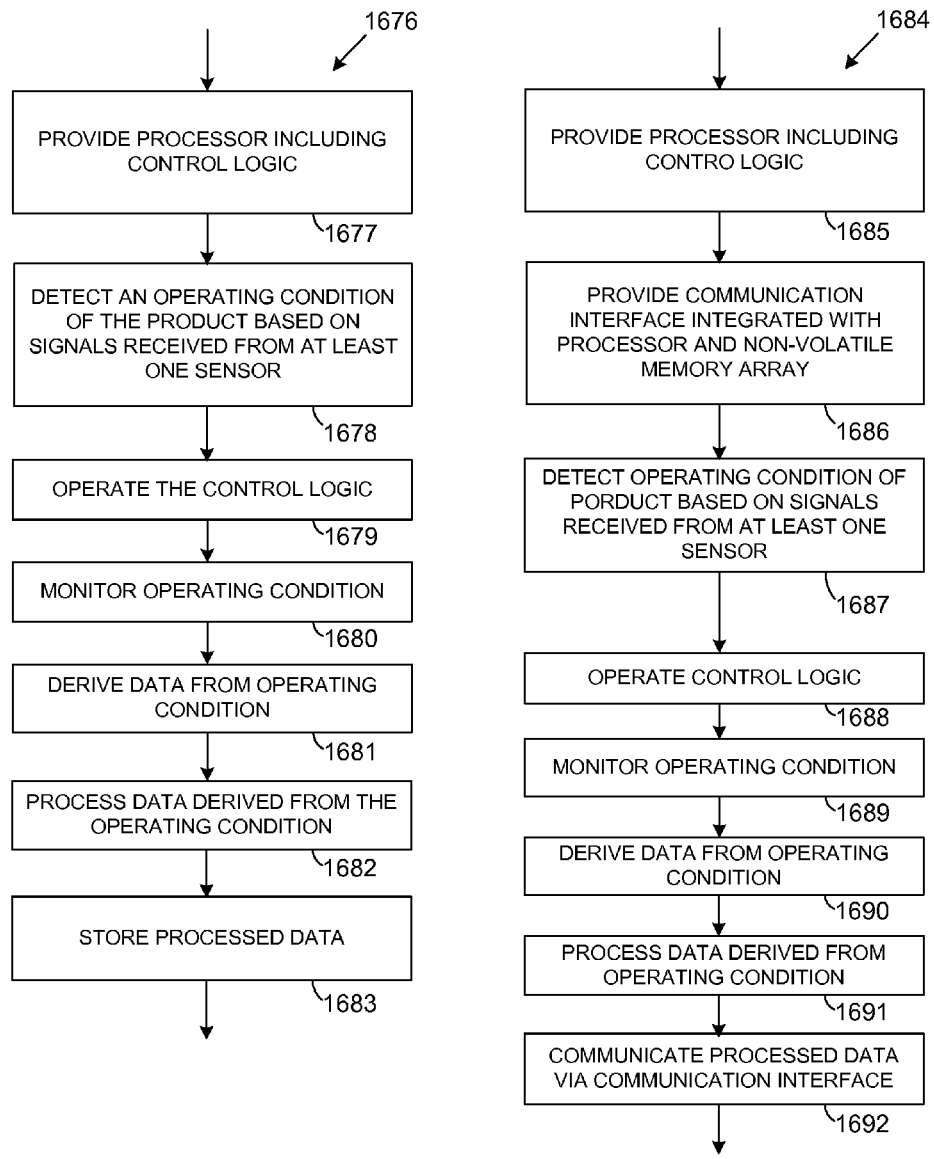

In various embodiments and/or applications, as shown in FIG. 16U, the method 1676 of operating the apparatus can further include providing 1677 the processor including control logic, detecting 1678 an operating condition of the product based on signals received from at least one sensor, and operating 1679 the control logic. Operating the processor 1679 can include monitoring 1680 the operating condition, deriving 1681 data from the operating condition, processing 1682 data derived from the operating condition, and storing 1683 the processed data.

As shown in FIG. 16V, in various embodiments and/or applications, the method 1684 of operating the apparatus can further be implemented to include providing 1685 the processor including control logic, providing 1686 a communication interface integrated with the processor and the non-volatile memory array, detecting 1687 an operating condition of the product based on signals received from at least one sensor, and operating 1688 the control logic. Operating 1688 the processor can include monitoring 1689 the operating condition, deriving 1690 data from the operating condition, processing 1691 data derived from the operating condition, and communicating 1692 the processed data via the communication interface.

Figures 17A, 17B:
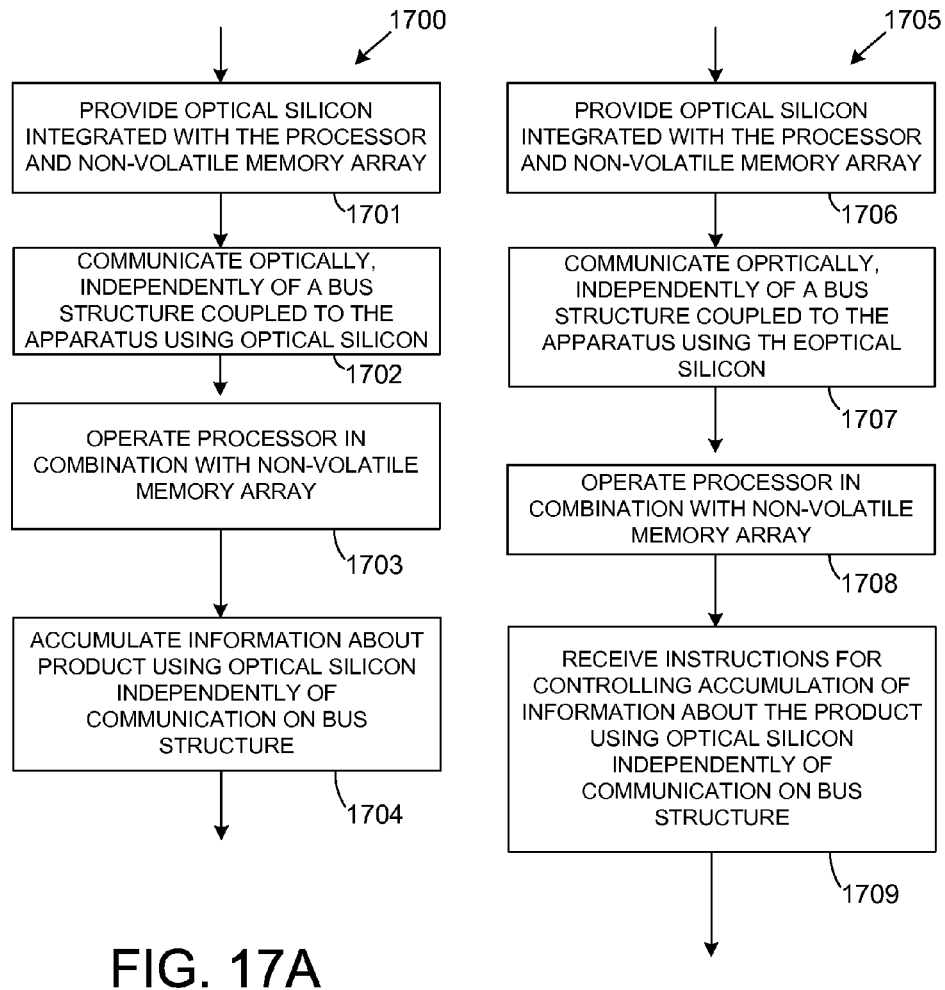

As illustrated in FIG. 17A, some embodiments of the method 1700 of operating the apparatus can further include providing 1701 optical silicon integrated with the processor and the non-volatile memory array, communicating 1702 optically, independently of a bus structure coupled to the apparatus using the optical silicon, and operating 1703 the processor in combination with the non-volatile memory array. Operating 1703 the processor in combination with the non-volatile memory array can include accumulating 1704 information about the product using the optical silicon independently of communication on the bus structure.

As shown in FIG. 17B, an embodiment of the method 1705 of operating the apparatus can further include providing 1706 optical silicon integrated with the processor and the non-volatile memory array, communicating 1707 optically, independently of a bus structure coupled to the apparatus using the optical silicon, and operating 1708 the processor in combination with the non-volatile memory array. Operating 1708 the processor in combination with the non-volatile memory array can include receiving 1709 instructions for controlling accumulation of information about the product using the optical silicon independently of communication on the bus structure.

Figure 18C:
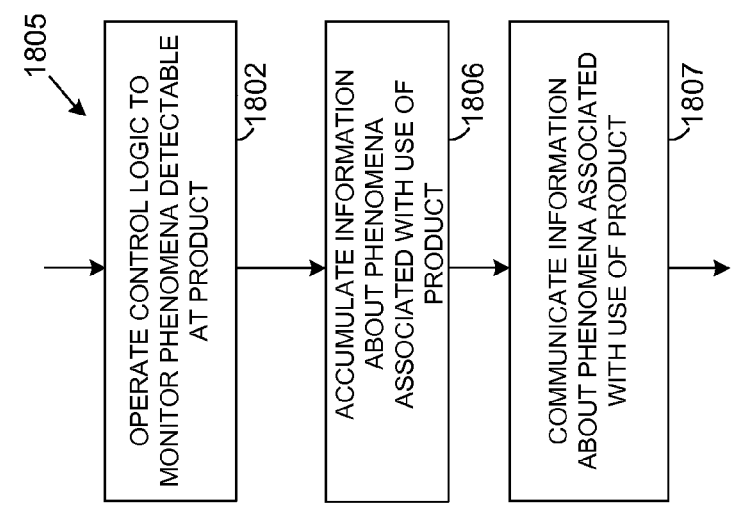

Referring to FIGS. 18A through 18M, multiple schematic flow charts show several embodiments and/or aspects of a method of operating an apparatus including control logic integrated with memory and further integrated into a product. The illustrative method 1800, depicted in FIG. 18A, of operating an apparatus can include providing 1801 a control logic integrated with and distributed over a non-volatile memory array and integrated into a product, and operating 1802 the control logic to monitor phenomena detectable at the product.

Figure 18B:
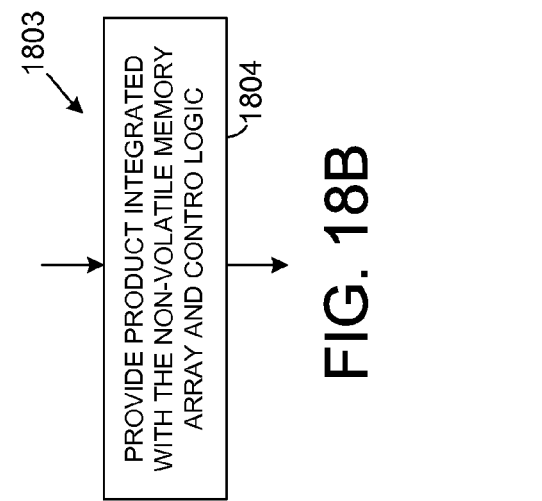
Figure 18A:
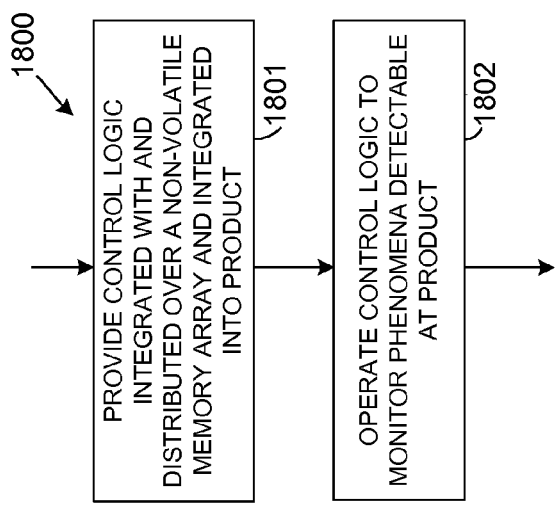

As shown in FIG. 18B, an embodiment of the method 1803 of operating the apparatus can be executed further including providing 1804 the product integrated with the non-volatile memory array and the control logic.

Referring to FIG. 18C, in some embodiments, the method 1805 of operating the apparatus can be configured such that operating 1802 the control logic to monitor phenomena detectable at the product includes accumulating 1806 information about phenomena associated with use of the product, and communicating 1807 the information about phenomena associated with use of the product.

Figures 18D, 18E, 18F:
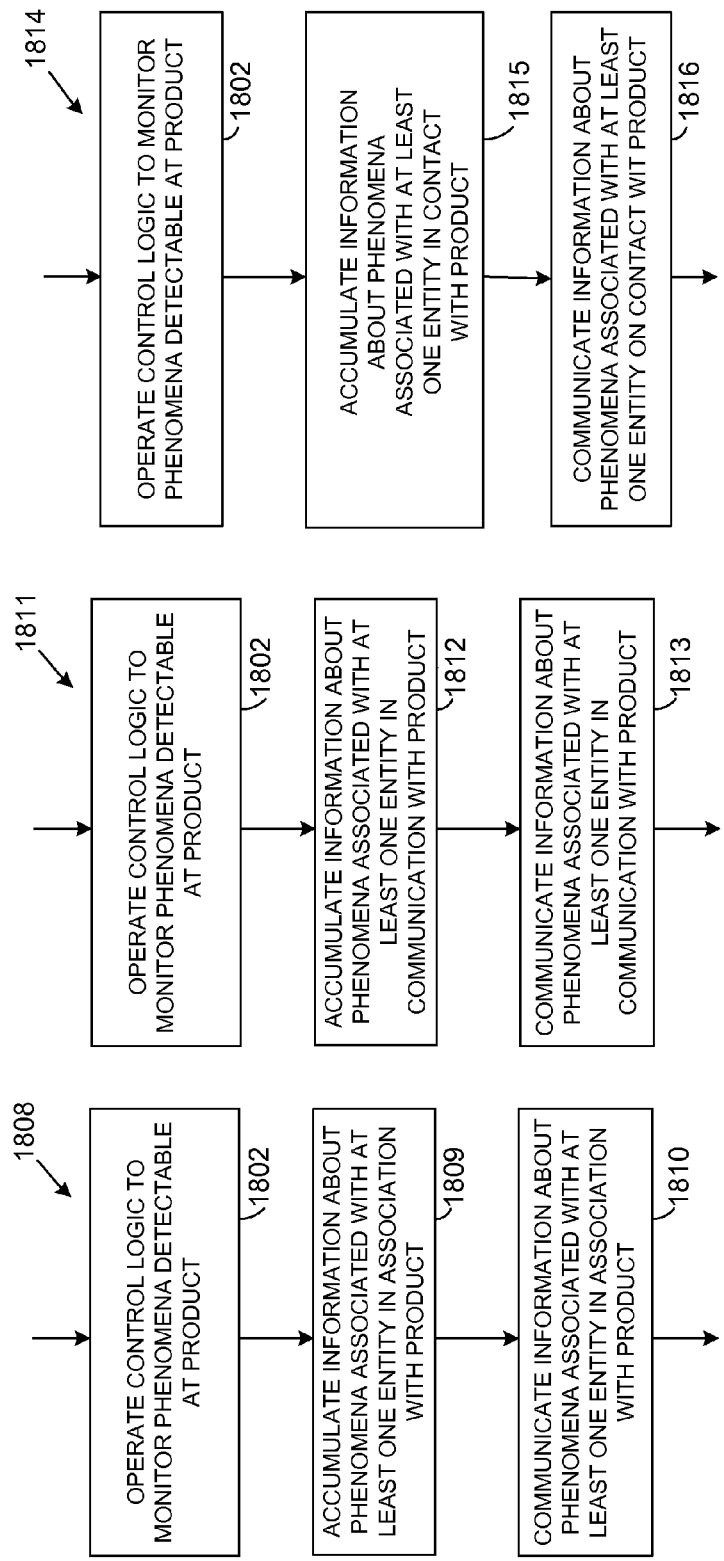

In further embodiments and/or applications, as shown in FIG. 18D, the method 1808 of operating the apparatus can be implemented so that operating 1802 the control logic to monitor phenomena detectable at the product includes accumulating 1809 information about phenomena associated with at least one entity in association with the product, and communicating 1810 the information about phenomena associated with at least one entity in association with the product.

In various embodiments, as depicted in FIG. 18E, the method 1811 of operating the apparatus can be arranged in a manner that operating 1802 the control logic to monitor phenomena detectable at the product includes accumulating 1812 information about phenomena associated with at least one entity in communication with the product, and communicating 1813 the information about phenomena associated with at least one entity in communication with the product.

In some embodiments, illustrated in FIG. 18F, the method 1814 of operating the apparatus can be composed such that operating 1802 the control logic to monitor phenomena detectable at the product includes accumulating 1815 information about phenomena associated with at least one entity in contact with the product, and communicating 1816 the information about phenomena associated with at least one entity in contact with the product.

As illustrated in FIG. 18G, some embodiments of the method 1817 of operating the apparatus can be performed with operating 1802 the control logic to monitor phenomena detectable at the product including monitoring 1818 tactile contact with the product.

In various embodiments and/or applications, as shown in FIG. 18H, the method 1819 of operating the apparatus can be configured such that operating 1802 the control logic to monitor phenomena detectable at the product includes monitoring 1818 tactile contact with the product, determining 1820 statistics on type, characteristics, and number of occurrences of tactile contact with the product, and storing 1821 the statistics for access.

Referring to FIG. 18I, selected embodiments of the method 1822 of operating the apparatus can be implemented so that operating 1802 the control logic to monitor phenomena detectable at the product includes monitoring 1823 conditions of the product independently of commands received from a source external to the product.

Figures 18J, 18K:
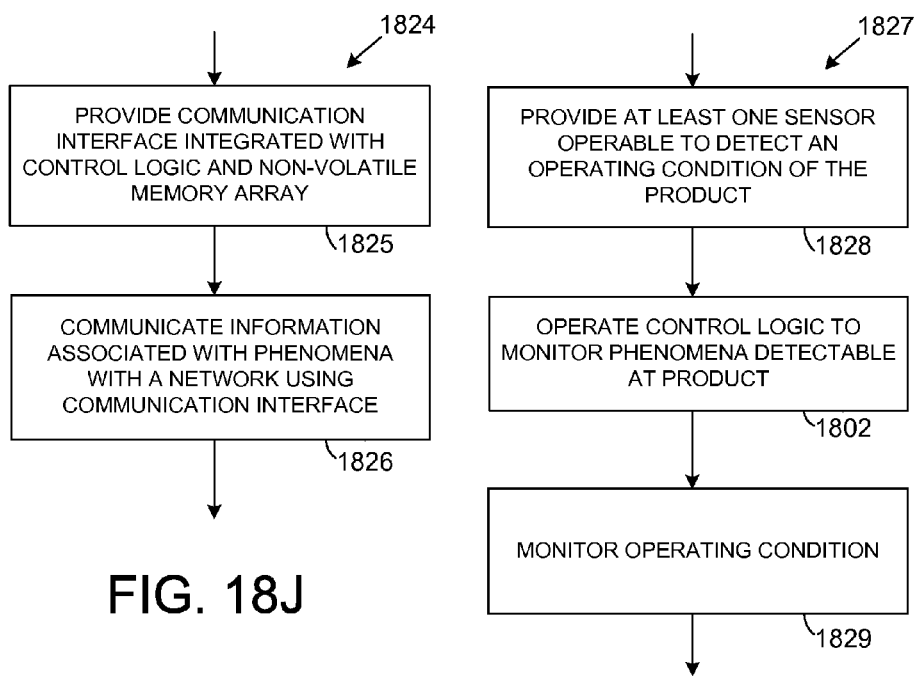

As illustrated in FIG. 18J, some embodiments of the method 1824 of operating the apparatus can further include providing 1825 a communication interface integrated with the control logic and the non-volatile memory array, and communicating 1826 information associated with the phenomena with a network using the communication interface.

As shown in FIG. 18K, an embodiment of the method 1827 of operating the apparatus can further include providing 1828 at least one sensor operable to detect an operating condition of the product, and operating 1802 the control logic to monitor phenomena detectable at the product which can include monitoring 1829 the operating condition.

Referring to FIG. 18L, in some embodiments, the method 1830 of operating the apparatus can further include providing 1828 at least one sensor operable to detect an operating condition of the product, and operating 1802 the control logic to monitor phenomena detectable at the product. Operating 1802 the control logic to monitor phenomena detectable at the product can include monitoring 1831 the operating condition, deriving 1832 data from the operating condition, processing 1833 data derived from the operating condition, and storing 1834 the processed data.

In further embodiments and/or applications, as shown in FIG. 18M, the method 1835 of operating the apparatus can further include providing 1836 a communication interface integrated with the control logic and the non-volatile memory array, and operating 1802 the control logic to monitor phenomena detectable at the product. Operating 1802 the control logic to monitor phenomena detectable at the product can include monitoring 1837 the operating condition, deriving 1838 data from the operating condition, processing 1839 data derived from the operating condition, and communicating 1840 the processed data via the communication interface.

Modules, logic, circuitry, hardware and software combinations, firmware, or so forth may be realized or implemented as one or more general-purpose processors, one or more processing cores, one or more special-purpose processors, one or more microprocessors, at least one Application-Specific Integrated Circuit (ASIC), at least one Field Programmable Gate Array (FPGA), at least one digital signal processor (DSP), some combination thereof, or so forth that is executing or is configured to execute instructions, a special-purpose program, an application, software, code, some combination thereof, or so forth as at least one special-purpose computing apparatus or specific computing component. One or more modules, logic, or circuitry, etc. may, by way of example but not limitation, be implemented using one processor or multiple processors that are configured to execute instructions (e.g., sequentially, in parallel, at least partially overlapping in a time-multiplexed fashion, at least partially overlapping across multiple cores, or a combination thereof, etc.) to perform a method or realize a particular computing machine. For example, a first module may be embodied by a given processor executing a first set of instructions at or during a first time, and a second module may be embodied by the same given processor executing a second set of instructions at or during a second time. Moreover, the first and second times may be at least partially interleaved or overlapping, such as in a multi-threading, pipelined, or predictive processing environment. As an alternative example, a first module may be embodied by a first processor executing a first set of instructions, and a second module may be embodied by a second processor executing a second set of instructions. As another alternative example, a particular module may be embodied partially by a first processor executing at least a portion of a particular set of instructions and embodied partially by a second processor executing at least a portion of the particular set of instructions. Other combinations of instructions, a program, an application, software, or code, etc. in conjunction with at least one processor or other execution machinery may be utilized to realize one or more modules, logic, or circuitry, etc. to implement any of the processing algorithms described herein.

Those having ordinary skill in the art will recognize that the state of the art has progressed to the point where there is little distinction left between hardware, software, and/or firmware implementations of aspects of systems; the use of hardware, software, and/or firmware is generally (but not always, in that in certain contexts the choice between hardware and software can become significant) a design choice representing cost vs. efficiency tradeoffs. Those having skill in the art will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those having ordinary skill in the art will recognize that optical aspects of implementations will typically employ optically-oriented hardware, software, and or firmware.

In some implementations described herein, logic and similar implementations may include software or other control structures suitable to operation. Electronic circuitry, for example, may manifest one or more paths of electrical current constructed and arranged to implement various logic functions as described herein. In some implementations, one or more media are configured to bear a device-detectable implementation if such media hold or transmit a special-purpose device instruction set operable to perform as described herein. In some variants, for example, this may manifest as an update or other modification of existing software or firmware, or of gate arrays or other programmable hardware, such as by performing a reception of or a transmission of one or more instructions in relation to one or more operations described herein. Alternatively or additionally, in some variants, an implementation may include special-purpose hardware, software, firmware components, and/or general-purpose components executing or otherwise invoking special-purpose components. Specifications or other implementations may be transmitted by one or more instances of tangible transmission media as described herein, optionally by packet transmission or otherwise by passing through distributed media at various times.

Alternatively or additionally, implementations may include executing a special-purpose instruction sequence or otherwise invoking circuitry for enabling, triggering, coordinating, requesting, or otherwise causing one or more occurrences of any functional operations described above. In some variants, operational or other logical descriptions herein may be expressed directly as source code and compiled or otherwise invoked as an executable instruction sequence. In some contexts, for example, C++ or other code sequences can be compiled directly or otherwise implemented in high-level descriptor languages (e.g., a logic-synthesizable language, a hardware description language, a hardware design simulation, and/or other such similar mode(s) of expression). Alternatively or additionally, some or all of the logical expression may be manifested as a Verilog-type hardware description or other circuitry model before physical implementation in hardware, especially for basic operations or timing-critical applications. Those having ordinary skill in the art will recognize how to obtain, configure, and optimize suitable transmission or computational elements, material supplies, actuators, or other common structures in light of these teachings.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those having ordinary skill in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those having ordinary skill in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link (e.g., transmitter, receiver, transmission logic, reception logic, etc.), etc.).

In a general sense, those having ordinary skill in the art will recognize that the various embodiments described herein can be implemented, individually and/or collectively, by various types of electro-mechanical systems having a wide range of electrical components such as hardware, software, firmware, and/or virtually any combination thereof; and a wide range of components that may impart mechanical force or motion such as rigid bodies, spring or torsional bodies, hydraulics, electro-magnetically actuated devices, and/or virtually any combination thereof. Consequently, as used herein "electro-mechanical system" includes, but is not limited to, electrical circuitry operably coupled with a transducer (e.g., an actuator, a motor, a piezoelectric crystal, a Micro Electro Mechanical System (MEMS), etc.), electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), electrical circuitry forming a communications device (e.g., a modem, communications switch, optical-electrical equipment, etc.), and/or any non-electrical analog thereto, such as optical or other analogs. Those having ordinary skill in the art will also appreciate that examples of electromechanical systems include but are not limited to a variety of consumer electronics systems, medical devices, as well as other systems such as motorized transport systems, factory automation systems, security systems, and/or communication/computing systems. Those having ordinary skill in the art will recognize that electro-mechanical as used herein is not necessarily limited to a system that has both electrical and mechanical actuation except as context may dictate otherwise.

In a general sense, those having ordinary skill in the art will recognize that the various aspects described herein which can be implemented, individually and/or collectively, by a wide range of hardware, software, firmware, and/or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), and/or electrical circuitry forming a communications device (e.g., a modem, communications switch, optical-electrical equipment, etc.). Those having skill in the art will recognize that the subject matter described herein may be implemented in an analog or digital fashion or some combination thereof.

Those having ordinary skill in the art will recognize that at least a portion of the devices and/or processes described herein can be integrated into an image processing system. Those having skill in the art will recognize that a typical image processing system generally includes one or more of a system unit housing, a video display device, memory such as volatile or non-volatile memory, processors such as microprocessors or digital signal processors, computational entities such as operating systems, drivers, applications programs, one or more interaction devices (e.g., a touch pad, a touch screen, an antenna, etc.), control systems including feedback loops and control motors (e.g., feedback for sensing lens position and/or velocity; control motors for moving/ distorting lenses to give desired focuses). An image processing system may be implemented utilizing suitable commercially available components, such as those typically found in digital still systems and/or digital motion systems.

Those having ordinary skill in the art will recognize that at least a portion of the devices and/or processes described herein can be integrated into a data processing system. Those having skill in the art will recognize that a data processing system generally includes one or more of a system unit housing, a video display device, memory such as volatile or non-volatile memory, processors such as microprocessors or digital signal processors, computational entities such as operating systems, drivers, graphical user interfaces, and applications programs, one or more interaction devices (e.g., a touch pad, a touch screen, an antenna, etc.), and/or control systems including feedback loops and control motors (e.g., feedback for sensing position and/or velocity; control motors for moving and/or adjusting components and/or quantities). A data processing system may be implemented utilizing suitable commercially available components, such as those typically found in data computing/communication and/or network computing/communication systems. Those having ordinary skill in the art will recognize that at least a portion of the devices and/or processes described herein can be integrated into a mote system. Those having skill in the art will recognize that a typical mote system generally includes one or more memories such as volatile or non-volatile memories, processors such as microprocessors or digital signal processors, computational entities such as operating systems, user interfaces, drivers, sensors, actuators, applications programs, one or more interaction devices (e.g., an antenna USB ports, acoustic ports, etc.), control systems including feedback loops and control motors (e.g., feedback for sensing or estimating position and/or velocity; control motors for moving and/or adjusting components and/or quantities). A mote system may be implemented utilizing suitable components, such as those found in mote computing/communication systems. Specific examples of such components entail such as Intel Corporation's and/or Crossbow Corporation's mote components and supporting hardware, software, and/or firmware.

Those having ordinary skill in the art will recognize that it is common within the art to implement devices and/or processes and/or systems, and thereafter use engineering and/or other practices to integrate such implemented devices and/or processes and/or systems into more comprehensive devices and/or processes and/or systems. That is, at least a portion of the devices and/or processes and/or systems described herein can be integrated into other devices and/or processes and/or systems via a reasonable amount of experimentation. Those having skill in the art will recognize that examples of such other devices and/or processes and/or systems might include—as appropriate to context and application—all or part of devices and/or processes and/or systems of (a) an air conveyance (e.g., an airplane, rocket, helicopter, etc.), (b) a ground conveyance (e.g., a car, truck, locomotive, tank, armored personnel carrier, etc.), (c) a building (e.g., a home, warehouse, office, etc.), (d) an appliance (e.g., a refrigerator, a washing machine, a dryer, etc.), (e) a communications system (e.g., a networked system, a telephone system, a Voice over IP system, etc.), (f) a business entity (e.g., an Internet Service Provider (ISP) entity such as Comcast Cable, Qwest, Southwestern Bell, etc.), or (g) a wired/wireless services entity (e.g., Sprint, Cingular, Nextel, etc.), etc.

In certain cases, use of a system or method may occur in a territory even if components are located outside the territory. For example, in a distributed computing context, use of a distributed computing system may occur in a territory even though parts of the system may be located outside of the territory (e.g., relay, server, processor, signal-bearing medium, transmitting computer, receiving computer, etc. located outside the territory). A sale of a system or method may likewise occur in a territory even if components of the system or method are located and/or used outside the territory. Further, implementation of at least part of a system for performing a method in one territory does not preclude use of the system in another territory.

One of ordinary skill in the art will recognize that the herein described components (e.g., operations), devices, objects, and the discussion accompanying them are used as examples for the sake of conceptual clarity and that various configuration modifications are contemplated. Consequently, as used herein, the specific exemplars set forth and the accompanying discussion are intended to be representative of their more general classes. In general, use of any specific exemplar is intended to be representative of its class, and the non-inclusion of specific components (e.g., operations), devices, and objects should not be taken limiting.

Those having ordinary skill in the art will appreciate that a user may be representative of a human user, a robotic user (e.g., computational entity), and/or substantially any combination thereof (e.g., a user may be assisted by one or more robotic agents) unless context dictates otherwise.

With respect to the use of substantially any plural and/or singular terms herein, those having skill in the art can translate from the plural to the singular and/or from the singular to the plural as is appropriate to the context and/or application. The various singular/plural permutations are not expressly set forth herein for sake of clarity. The herein described subject matter sometimes illustrates different components contained within, or connected with, different other components. It is to be understood that such depicted architectures are merely exemplary, and that in fact many other architectures may be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components, and/or wirelessly interactable, and/or wirelessly interacting components, and/or logically interacting, and/or logically interactable components.

In some instances, one or more components may be referred to herein as "configured to," "configurable to," "operable/operative to," "adapted/adaptable," "able to," "conformable/conformed to," etc. Those having ordinary skill in the art will recognize that "configured to" can generally encompass active-state components and/or inactive-state components and/or standby-state components, unless context requires otherwise. While particular aspects of the present subject matter described herein have been shown and described, it will be apparent to those having ordinary skill in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those having ordinary skill in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms. For example, the phrase "A or B" will be typically understood to include the possibilities of "A" or "B" or "A and B."

With respect to the appended claims, those having ordinary skill in the art will appreciate that recited operations therein may generally be performed in any order. Also, although various operational flows are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

What is claimed is:

1. An apparatus comprising:
a flexible biodegradable substrate configured to conform to at least one of internal or surface biological tissue;
one or more non-volatile memory arrays configured as flexible biodegradable memory formed of biodegradable circuit components integrated onto the flexible biodegradable substrate; and
one or more processors configured as a flexible biodegradable integrated circuit formed of biodegradable circuit components integrated onto and distributed spatially and functionally over the one or more non-volatile memory arrays and integrated onto the flexible biodegradable substrate, the one or more processors configured to accumulate information relating at least in part to contact with the internal or surface biological tissue, wherein the flexible biodegradable integrated circuit integrated onto the flexible biodegradable substrate, the one or more non-volatile memory arrays, and the one or more processors are configured in a flexible structure that conforms to the at least one of internal or surface biological tissue.

2. The apparatus according to claim 1 further comprising:
a medical device integrated with the flexible biodegradable substrate, the one or more non-volatile memory arrays and the one or more processors configured for implantable or external contact with the at least one of internal or surface biological tissue.

3. The apparatus according to claim 1 further comprising:
a product integrated with the flexible biodegradable substrate, the one or more non-volatile memory arrays and the one or more processors; wherein:
the one or more processors are configured to accumulate and communicate information about use of the product integrated with the flexible biodegradable substrate, the one or more non-volatile memory arrays, and the one or more processors.

4. The apparatus according to claim 1 further comprising:
a product integrated with the flexible biodegradable substrate, the one or more non-volatile memory arrays and the one or more processors; wherein:
the one or more processors are configured to accumulate and communicate information about at least one biological entity in association with the product integrated with the flexible biodegradable substrate, the one or more non-volatile memory arrays, and the one or more processors.

5. The apparatus according to claim 1 further comprising:
a product integrated with the flexible biodegradable substrate, the one or more non-volatile memory arrays and the one or more processors; wherein:
the one or more processors are configured to accumulate and communicate information about at least one biological entity in communication with the product integrated with the flexible biodegradable substrate, the one or more non-volatile memory arrays, and the one or more processors.

6. The apparatus according to claim 1 further comprising:
a product integrated with the flexible biodegradable substrate, the one or more non-volatile memory arrays and the one or more processors; wherein:
the one or more processors are configured to accumulate and communicate information about at least one biological entity in contact with the product integrated with the flexible biodegradable substrate, the one or more non-volatile memory arrays, and the one or more processors.

7. The apparatus according to claim 1 further comprising:
a product integrated with the flexible biodegradable substrate, the one or more non-volatile memory arrays and the one or more processors; wherein:
the flexible biodegradable substrate, the one or more processors, and the one or more non-volatile memory arrays are integrated onto a printed polymer for integration with the product integrated with the flexible biodegradable substrate, the one or more non-volatile memory arrays, and the one or more processors.

8. The apparatus according to claim 1 further comprising:
a product integrated with the flexible biodegradable substrate, the one or more non-volatile memory arrays and the one or more processors; wherein:
the flexible biodegradable substrate, the one or more processors, and the one or more non-volatile memory arrays are integrated onto a printed flexible polymer for integration with the product integrated with the flexible biodegradable substrate, the one or more non-volatile memory arrays, and the one or more processors.

9. The apparatus according to claim 1 further comprising:
a communication interface integrated with the one or more processors, and the one or more non-volatile memory arrays, the communication interface operable for communication with a network.

10. The apparatus according to claim 1 further comprising:
a communication interface integrated with the one or more processors, and the one or more non-volatile memory arrays, the communication interface operable for communication with a network wherein:
the one or more processors are configured to perform data preprocessing, history tracking, and manage data and history communication associated with the accumulated information relating at least in part to contact with the at least one of internal or surface biological tissue.

11. The apparatus according to claim 1 further comprising:
one or more volatile memories integrated onto the flexible biodegradable substrate, the one or more non-volatile memory arrays and the one or more processors.

12. The apparatus according to claim 1 wherein:
the one or more processors are configured to monitor tactile contact of the at least one of internal or surface biological tissue with a product integrated with the flexible biodegradable substrate, the one or more non-volatile memory arrays, and the one or more processors.

13. The apparatus according to claim 1 further comprising:
a product integrated with the flexible biodegradable substrate, the one or more non-volatile memory arrays and the one or more processors; wherein:
the one or more processors are configured to monitor tactile contact of the at least one of internal or surface biological tissue with the product integrated with the flexible biodegradable substrate, the one or more non-volatile memory arrays, and the one or more processors, determine statistics on type, characteristics, and number of occurrences of tactile contact of the at least one of internal or surface biological tissue with the product integrated with the flexible biodegradable substrate, the one or more non-volatile memory arrays, and the one or more processors, and store the statistics for access.

14. The apparatus according to claim 1 further comprising:
a product integrated with the flexible biodegradable substrate, the one or more non-volatile memory arrays and the one or more processors; wherein:
the one or more processors are configured to monitor conditions of the product integrated with the flexible biodegradable substrate, the one or more non-volatile memory arrays, and the one or more processors independently of commands received from a source external to the product integrated with the flexible biodegradable substrate, the one or more non-volatile memory arrays, and the one or more processors.

15. The apparatus according to claim 1 wherein:
the one or more non-volatile memory arrays is partitioned into a plurality of memory blocks; and
the one or more processors include biodegradable control logic partitioned into a plurality of command logic blocks spatially distributed over the one or more non-volatile memory arrays wherein one or more of the plurality of command logic block are associated with ones of the plurality of memory blocks.

16. The apparatus according to claim 1 wherein:
the one or more processors includes two or more portions of biodegradable control logic integrated onto and distributed over two or more portions of the one or more non-volatile memory arrays, the biodegradable control logic operable to selectively distribute functionality across respective two or more portions of the one or more non-volatile memory arrays.

17. The apparatus according to claim 1 wherein:
the one or more non-volatile memory arrays include a plurality of memory blocks characterized by a plurality of different operating characteristics; and
the one or more processors include two or more portions of biodegradable control logic operable to selectively distribute functionality over respective two or more portions of the plurality of memory blocks.

18. The apparatus according to claim 1 wherein:
the one or more non-volatile memory arrays include a plurality of memory blocks characterized by a plurality of different operating characteristics; and
the one or more processors includes two or more portions of biodegradable control logic operable to analyze conditions of the product integrated with the flexible biodegradable substrate, the one or more non-volatile memory arrays, and the one or more processors and selectively distribute functionality over respective two or more portions of the plurality of memory blocks based on the analysis.

19. The apparatus according to claim 1 further comprising:
at least one sensor operable to detect an operating condition of at least one of the flexible biodegradable substrate, the one or more non-volatile memory arrays, or the one or more processors, wherein:
the one or more processors include biodegradable control logic operable to monitor the operating condition.

20. The apparatus according to claim 1 further comprising:
at least one sensor operable to detect an operating condition of at least one of the flexible biodegradable substrate, the one or more non-volatile memory arrays, and the one or more processors, wherein:
the one or more processors include biodegradable control logic operable to monitor the operating condition, derive data derived from the operating condition, process data derived from the operating condition, and store the processed data.

21. The apparatus according to claim 1 further comprising:
a communication interface integrated with the one or more processors, and the one or more non-volatile memory arrays; and
at least one sensor operable to detect an operating condition of at least one of the flexible biodegradable substrate, the one or more non-volatile memory arrays, and the one or more processors, wherein:
the one or more processors include biodegradable control logic operable to monitor the operating condition, derive data from the operating condition, process data derived from the operating condition, and communicate the processed data via the communication interface.

22. The apparatus according to claim 1 further comprising:
optical silicon operable to communicate optically, independently of a bus structure coupled to the apparatus wherein:
the one or more processors are configured to operate in combination with the one or more non-volatile memory arrays to accumulate information about at least one of the flexible biodegradable substrate, the one or more non-volatile memory arrays, and the one or more processors using the optical silicon independently of communication on the bus structure.

23. The apparatus according to claim 1 further comprising:
optical silicon operable to communicate optically, independently of a bus structure coupled to the apparatus wherein:
the one or more processors are configured to operate in combination with the one or more non-volatile memory arrays to receive instructions for controlling accumulation of information about at least one of the flexible biodegradable substrate, the one or more non-volatile memory arrays, and the one or more processors using the optical silicon independently of communication on the bus structure.

24. The apparatus according to claim 1 further comprising:
a medical device configured as a medical support material that is dissolvable in a patient's body integrated with the flexible biodegradable substrate, the one or more non-volatile memory arrays and the one or more processors.

25. The apparatus according to claim 1 further comprising:
a Transcutaneous Electrical Nerve Stimulation (TENS) device integrated with the flexible biodegradable substrate, the one or more non-volatile memory arrays and the one or more processors, wherein the TENS device includes one or more electrodes formed on the flexible biodegradable substrate.

26. The apparatus according to claim 1 further comprising:
a biocompatible, biodegradable hemodynamic monitor integrated with the flexible biodegradable substrate, the one or more non-volatile memory arrays and the one or more processors, wherein the biocompatible, biodegradable hemodynamic monitor is configured for implantable or external use in contact in conformation with the at least one of internal or surface biological tissue.

27. The apparatus according to claim 1 further comprising:
a flexible identification armband integrated with the flexible biodegradable substrate, the one or more non-volatile memory arrays and the one or more processors, wherein the flexible identification armband is configured for performing security operations in a location.

28. The apparatus according to claim 1 further comprising:
a medical device sleeve integrated with the flexible biodegradable substrate, the one or more non-volatile memory arrays and the one or more processors, wherein the medical device sleeve is configured for monitoring implanted medical devices including knee implants, hip implants, shoulder implants, elbow implants, or cardiovascular implants.

29. An apparatus comprising:
a flexible biodegradable substrate configured to conform to at least one of internal or surface biological tissue;
one or more non-volatile memory arrays configured as flexible biodegradable memory formed of biodegradable circuit components integrated into the flexible biodegradable substrate; and
biodegradable control logic formed of biodegradable circuit components integrated onto and distributed spatially and functionally over the one or more non-volatile memory arrays into the flexible biodegradable substrate in a flexible biodegradable integrated circuit, the biodegradable control logic including multiple portions configured to distribute functionality over respective portions of the one or more non-volatile memory arrays at least in part to monitor phenomena relating at least in part to contact with the at least one of internal or surface biological tissue, wherein the flexible biodegradable integrated circuit integrated onto the flexible biodegradable substrate, the one or more non-volatile memory arrays, and the biodegradable control logic are configured in a flexible structure that conforms to the at least one of internal or surface biological tissue.

30. The apparatus according to claim 29 further comprising:
a medical device integrated with the flexible biodegradable substrate, the one or more non-volatile memory arrays and the biodegradable control logic configured for implantable or external contact with the at least one of internal or surface biological tissue.

31. The apparatus according to claim 29, further comprising:
a product integrated with the flexible biodegradable substrate, the one or more non-volatile memory arrays and the biodegradable control logic; wherein:
the biodegradable control logic is operable to accumulate and communicate information about phenomena relating at least in part to contact with the at least one of internal or surface biological tissue associated with use of the product integrated with the flexible biodegradable substrate, the one or more non-volatile memory arrays, and the biodegradable control logic.

32. The apparatus according to claim 29, further comprising:
a product integrated with the flexible biodegradable substrate, the one or more non-volatile memory arrays and the biodegradable control logic; wherein:
the biodegradable control logic is operable to accumulate and communicate information about phenomena relating at least in part to contact with the at least one of internal or surface biological tissue associated with at least one biological entity in contact with the product integrated with the flexible biodegradable substrate, the one or more non-volatile memory arrays, and the biodegradable control logic.

33. The apparatus according to claim 29, further comprising:
a product integrated with the flexible biodegradable substrate, the one or more non-volatile memory arrays and the biodegradable control logic; wherein:
the biodegradable control logic is operable to accumulate and communicate information about phenomena relating at least in part to contact with the at least one of internal or surface biological tissue associated with at least one biological entity in communication with the product integrated with the flexible biodegradable substrate, the one or more non-volatile memory arrays, and the biodegradable control logic.

34. The apparatus according to claim 29, further comprising:
a product integrated with the flexible biodegradable substrate, the one or more non-volatile memory arrays and the biodegradable control logic; wherein:
the biodegradable control logic is operable to accumulate and communicate information about phenomena relating at least in part to contact with the at least one of internal or surface biological tissue associated with at least one biological entity in contact with the product integrated with the flexible biodegradable substrate, the one or more non-volatile memory arrays, and the biodegradable control logic.

35. The apparatus according to claim 29, further comprising:
a product integrated with the flexible biodegradable substrate, the one or more non-volatile memory arrays and the biodegradable control logic; wherein:
the biodegradable control logic is operable to monitor tactile contact of the at least one of internal or surface biological tissue with the product integrated with the flexible biodegradable substrate, the one or more non-volatile memory arrays, and the biodegradable control logic.

36. The apparatus according to claim 29, further comprising:
a product integrated with the flexible biodegradable substrate, the one or more non-volatile memory arrays and the biodegradable control logic; wherein:
the biodegradable control logic is operable to monitor tactile contact of the at least one of internal or surface biological tissue with the product integrated with the flexible biodegradable substrate, the one or more non-volatile memory arrays, and the biodegradable control logic, determine statistics on type, characteristics, and number of occurrences of tactile contact of the at least one of internal or surface biological tissue with the product integrated with the flexible biodegradable substrate, the one or more non-volatile memory arrays, and the biodegradable control logic, and store the statistics for access.

37. The apparatus according to claim 29, further comprising:

a product integrated with the flexible biodegradable substrate, the one or more non-volatile memory arrays and the biodegradable control logic; wherein:

the biodegradable control logic is operable to monitor conditions of the product integrated with the flexible biodegradable substrate, the one or more non-volatile memory arrays, and the biodegradable control logic independently of commands received from a source external to the product integrated with the flexible biodegradable substrate, the one or more non-volatile memory arrays, and the biodegradable control logic.

38. The apparatus according to claim 29 further comprising:

a communication interface integrated with the biodegradable control logic and the one or more non-volatile memory arrays, the communication interface operable for communicating information associated with the phenomena relating at least in part to contact with the at least one of internal or surface biological tissue and with a network.

39. The apparatus according to claim 29 further comprising:

a product integrated with the flexible biodegradable substrate, the one or more non-volatile memory arrays and the biodegradable control logic; and at least one sensor operable to detect an operating condition of the product integrated with the flexible biodegradable substrate, the one or more non-volatile memory arrays, and the biodegradable control logic; wherein:

the biodegradable control logic is operable to monitor the operating condition and phenomena relating at least in part to contact with the at least one of internal or surface biological tissue and detectable at the product integrated with the flexible biodegradable substrate, the one or more non-volatile memory arrays.

40. The apparatus according to claim 29 further comprising:

a product integrated with the flexible biodegradable substrate, the one or more non-volatile memory arrays and the biodegradable control logic; and at least one sensor operable to detect an operating condition of the product integrated with the flexible biodegradable substrate, the one or more non-volatile memory arrays, and the biodegradable control logic; wherein:

the biodegradable control logic is operable to monitor phenomena relating at least in part to contact with the at least one of internal or surface biological tissue and detectable at the product integrated with the flexible biodegradable substrate, the one or more non-volatile memory arrays, wherein the biodegradable control logic is further operable to monitor the operating condition, derive data from the operating condition, process data derived from the operating condition, and store the processed data.

41. The apparatus according to claim 29 further comprising:

a product integrated with the flexible biodegradable substrate, the one or more non-volatile memory arrays and the biodegradable control logic;

a communication interface integrated with the biodegradable control logic and the one or more non-volatile memory arrays; and at least one sensor operable to detect an operating condition of the product integrated with the flexible biodegradable substrate, the one or more non-volatile memory arrays, and the biodegradable control logic, wherein:

the biodegradable control logic is operable to monitor phenomena relating at least in part to contact with the at least one of internal or surface biological tissue and detectable at the product integrated with the flexible biodegradable substrate, the one or more non-volatile memory arrays, and the biodegradable control logic is further operable to monitor the operating condition, derive data from the operating condition, process data derived from the operating condition, and communicate the processed data via the communication interface.

42. An information handling system comprising:

means for supporting an integrated circuit;

means for storing information for at least read access integrated onto the means for supporting the integrated circuit; and means for executing information handling functions integrated onto the means for supporting the integrated circuit and distributed spatially and functionally over the means for storing information, the means for executing information handling functions including multiple portions configured to distribute functionality over respective portions of the means for storing information; wherein means for executing information handling functions includes at least:

means for accumulating information relating at least in part to contact in conformation with the at least one of internal or surface biological tissue; wherein:

the means for supporting an integrated circuit is biodegradable and configured in a flexible structure that conforms to at least one of internal or surface biological tissue, and the means for storing information and the means for executing information handling functions are biodegradable, formed of biodegradable circuit components, and configured in a flexible structure that conforms to at least one of internal or surface biological tissue.

* * * * *